US012589094B2

(12) United States Patent
Hunt et al.

(10) Patent No.: US 12,589,094 B2
(45) **Date of Patent: *Mar. 31, 2026**

(54) CONCOMITANT ADMINISTRATION OF GLUCOCORTICOID RECEPTOR MODULATOR RELACORILANT AND PACLITAXEL, A DUAL SUBSTRATE OF CYP2C8 AND CYP3A4

(71) Applicant: Corcept Therapeutics Incorporated, Menlo Park, CA (US)

(72) Inventors: Hazel Hunt, Storrington (GB); Joseph Custodio, Menlo Park, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,002

(22) Filed: Feb. 28, 2024

(65) Prior Publication Data

US 2024/0261277 A1 Aug. 8, 2024

Related U.S. Application Data

(63) Continuation of application No. 17/672,380, filed on Feb. 15, 2022, now Pat. No. 11,944,617, which is a continuation of application No. 17/331,130, filed on May 26, 2021, now Pat. No. 11,285,145.

(60) Provisional application No. 63/030,800, filed on May 27, 2020.

(51) Int. Cl.
*A61K 31/4725* (2006.01)
*A61K 31/337* (2006.01)
*A61P 35/00* (2006.01)

(52) U.S. Cl.
CPC ........ *A61K 31/4725* (2013.01); *A61K 31/337* (2013.01); *A61P 35/00* (2018.01)

(58) Field of Classification Search
CPC .. A61K 31/416; A61K 31/445; A61K 31/451; A61K 31/4725; A61K 31/337; A61P 35/00
See application file for complete search history.

(56) References Cited

U.S. PATENT DOCUMENTS 4,963,558 A 10/1990 Hotten et al.
5,696,127 A 12/1997 Jones et al.
6,166,013 A 12/2000 Coghlan et al.
6,583,180 B2 6/2003 Link et al.
6,680,310 B2 1/2004 Belanoff et al.
7,576,076 B2 8/2009 Clark et al.
7,678,813 B2 3/2010 Clark et al.
7,790,745 B2 9/2010 Yang et al.
7,799,782 B2 9/2010 Munson et al.
7,928,237 B2 4/2011 Clark et al.
8,003,689 B2 8/2011 Veverka
8,173,674 B2 5/2012 Keil et al.
8,324,203 B2 12/2012 Clark et al.
8,461,172 B2 6/2013 Clark et al.
8,557,839 B2 10/2013 Clark et al.
8,598,149 B2 12/2013 Belanoff
8,598,154 B2 12/2013 Clark et al.
8,658,128 B2 2/2014 Altschul et al.
8,685,973 B2 4/2014 Clark et al.
8,710,035 B2 4/2014 Pan et al.
8,859,774 B2 10/2014 Hunt et al.
8,889,867 B2 11/2014 Clark et al.
8,921,348 B2 12/2014 Belanoff
8,969,557 B2 3/2015 Harriman et al.
9,107,926 B2 8/2015 Belvin et al.
(Continued)

FOREIGN PATENT DOCUMENTS

AU 2009267016 B2 7/2014
AU 2014352915 B2 6/2018
(Continued)

OTHER PUBLICATIONS

Custodio et al., "An In Vitro and In Vivo Evaluation of the Effect of Relacorilant on the Activity of Cytochrome P450 Drug Metabolizing Enzymes", The Journal of Clinical Pharmacology, vol. 61, No. 2, Feb. 2021, pp. 244-253.
European Patent Application No. 21813619.0 , "Extended European Search Report", May 10, 2024, 9 pages.
Hunt et al., "Identification of the Clinical Candidate (R)-(1-(4-Fluorophenyl)-6-((1-Methyl-1H-Pyrazol-4-yl)Sulfonyl)-4,4a,5,6,7,8-Hexahydro-1H-Pyrazolo[3,4-g]Isoquinolin-4a-yl)(4-(Trifluoromethyl)Pyridin-2-yl)Methanone (CORT125134): A Selective Glucocorticoid Receptor", (GR) Antagonist, Journal of Medicinal Chemistry, vol. 60, No. 8, Apr. 3, 2017, pp. 3405-3421.
(Continued)

*Primary Examiner* — George W Kosturko
(74) *Attorney, Agent, or Firm* — James Fox; Kilpatrick Townsend & Stockon LLP

(57) ABSTRACT

Many drugs useful in treating cancer are metabolized by CYP2C8 enzymes, by CYP3A4 enzymes, or both. The effects of concomitant administration of relacorilant and paclitaxel, a drug used to treat cancer that is a substrate for both CYP2C8 and CYP3A4, are disclosed herein.
Relacorilant potently inhibited CYP2C8 and CYP3A4 in in vitro tests, indicating that co-administration of relacorilant and paclitaxel would increase paclitaxel plasma exposure more than 5-fold in vivo, requiring significant reductions in paclitaxel doses when co-administering paclitaxel with relacorilant.
Surprisingly, paclitaxel plasma exposure increased only by about 80% instead of the expected more than 5-fold increase expected with concomitant relacorilant and paclitaxel administration. Applicant discloses safe methods of co-administering relacorilant and paclitaxel by reducing the dose of paclitaxel to about half the paclitaxel dose used when paclitaxel is administered alone. Relacorilant and such reduced doses of paclitaxel may be co-administered to treat cancer, e.g., ovarian or pancreatic cancer.

13 Claims, 1 Drawing Sheet

(56) References Cited

U.S. PATENT DOCUMENTS 9,114,147 B2 8/2015 Altschul et al.
9,149,485 B2 10/2015 Pan et al.
9,216,221 B2 12/2015 Newell-Price
9,273,047 B2 3/2016 Hunt et al.
9,289,436 B2 3/2016 Szmulewitz et al.
9,314,473 B2 4/2016 Altschul et al.
9,320,747 B1 4/2016 Altschul et al.
9,422,323 B2 8/2016 Houpis et al.
9,623,032 B2 4/2017 Pan et al.
9,707,223 B2 7/2017 Hunt et al.
9,801,893 B2 10/2017 Szmulewitz et al.
9,829,495 B2 11/2017 Moraitis
9,942,505 B2 4/2018 Nitta et al.
9,943,505 B2 * 4/2018 Hunt .................. A61K 31/7068
9,943,526 B2 4/2018 Belanoff et al.
9,956,216 B2 5/2018 Hunt et al.
10,047,082 B2 8/2018 Hunt et al.
10,117,852 B2 11/2018 Hunt et al.
10,151,763 B2 12/2018 Moraitis
10,195,214 B2 2/2019 Belanoff
10,213,414 B2 * 2/2019 Hunt ....................... A61P 35/00
10,323,034 B2 6/2019 Hunt et al.
10,413,540 B2 9/2019 Hunt
10,441,596 B2 10/2019 Pan et al.
10,449,178 B2 10/2019 Hunt et al.
10,456,392 B2 10/2019 Hunt et al.
10,568,880 B2 2/2020 Hunt
10,646,474 B2 * 5/2020 Hunt ...................... A61K 31/44
10,828,280 B2 * 11/2020 Hunt ...................... A61K 45/06
10,842,800 B2 11/2020 Belanoff
10,898,478 B2 1/2021 Hunt
10,973,813 B2 * 4/2021 Hunt .................. A61K 31/5377
10,980,797 B2 4/2021 Hunt
11,058,670 B2 7/2021 Moraitis
11,202,784 B2 12/2021 Moraitis et al.
11,285,145 B2 * 3/2022 Hunt .................... A61K 31/337
11,327,083 B2 5/2022 Moraitis
11,464,764 B2 10/2022 Scott et al.
11,560,379 B2 1/2023 Hunt et al.
11,590,113 B2 2/2023 Moraitis
11,642,331 B2 * 5/2023 Hunt ....................... A61P 43/00
514/405
11,660,295 B2 5/2023 Hunt
11,684,612 B2 6/2023 Moraitis
11,744,837 B2 9/2023 Moraitis
11,890,289 B2 2/2024 Moraitis et al.
11,925,626 B2 3/2024 Scott et al.
11,944,617 B2 * 4/2024 Hunt .................. A61K 31/4725
12,285,425 B2 4/2025 Hunt
12,514,849 B2 1/2026 Scott et al.
2002/0115613 A1 8/2002 Kumar
2003/0064974 A1 4/2003 Belanoff
2004/0029848 A1 2/2004 Belanoff
2004/0102422 A1 5/2004 Gaston
2004/0229855 A1 11/2004 Belanoff
2005/0085464 A1 4/2005 Sapse et al.
2005/0124533 A1 6/2005 Schatzberg et al.
2005/0245588 A1 11/2005 Ali et al.
2006/0063748 A1 3/2006 Belanoff
2006/0223852 A1 10/2006 Gillespie et al.
2007/0128627 A1 6/2007 Simons et al.
2007/0203179 A1 8/2007 Clark et al.
2007/0254025 A1 11/2007 Cronk
2007/0281928 A1 12/2007 Clark et al.
2008/0070950 A1 3/2008 Benjamin et al.
2008/0287419 A1 11/2008 Bruncko et al.
2009/0047365 A1 2/2009 Owa et al.
2009/0156672 A1 6/2009 Budunova et al.
2010/0135956 A1 6/2010 Gant et al.
2010/0179115 A1 7/2010 Belanoff
2010/0261693 A1 10/2010 Ulmann et al.
2010/0292477 A1 11/2010 Clark et al.
2011/0166110 A1 7/2011 Clark et al.
2011/0166115 A1 7/2011 Belanoff
2011/0269728 A1 11/2011 Pan et al.
2012/0022121 A1 1/2012 Dalton et al.
2012/0142913 A1 6/2012 Kamal et al.
2012/0201747 A1 8/2012 Altschul et al.
2012/0220565 A1 8/2012 Clark et al.
2012/0238549 A1 9/2012 Cusack et al.
2013/0225633 A1 8/2013 Hunt et al.
2014/0005158 A1 1/2014 Belanoff
2014/0038926 A1 2/2014 Hunt et al.
2014/0186367 A1 7/2014 Pan et al.
2014/0315866 A1 10/2014 Pan et al.
2014/0341849 A1 11/2014 Pan et al.
2015/0010503 A1 1/2015 Szmulewitz et al.
2015/0080389 A1 3/2015 Hunt et al.
2015/0118244 A1 4/2015 Shahabi et al.
2015/0148341 A1 5/2015 Hunt et al.
2015/0196640 A1 7/2015 Cacase et al.
2015/0346210 A1 12/2015 Nitta et al.
2016/0067264 A1 3/2016 Newell-Price
2016/0151388 A1 6/2016 Szmulewitz et al.
2016/0215049 A1 7/2016 Feldhaus et al.
2017/0020860 A1 1/2017 Hunt et al.
2017/0087120 A1 3/2017 Sachdeva et al.
2017/0182066 A1 6/2017 Pan et al.
2017/0273972 A1 9/2017 Hunt et al.
2017/0281651 A1 10/2017 Belanoff
2017/0326157 A1 11/2017 Belanoff
2018/0036318 A1 2/2018 Szmulewitz et al.
2018/0071255 A1 * 3/2018 Hunt ....................... A61P 35/00
2018/0125856 A1 5/2018 Moraitis et al.
2018/0193313 A1 7/2018 Hunt et al.
2018/0280378 A1 * 10/2018 Hunt .................. A61K 31/4745
2018/0325891 A1 11/2018 Scott
2019/0076424 A1 3/2019 Hunt
2020/0147065 A1 5/2020 Moraitis
2020/0197372 A1 6/2020 Scott et al.
2021/0128584 A1 5/2021 Belanoff
2021/0169872 A1 6/2021 Hunt et al.
2021/0369700 A1 12/2021 Hunt et al.
2021/0369701 A1 12/2021 Hunt et al.

FOREIGN PATENT DOCUMENTS

CA 2931302 A1 5/2015
CL 2014001241 A1 11/2014
CL 2014003162 A1 2/2015
CL 56987 12/2018
CN 101027301 A 8/2007
CN 101119970 A 2/2008
CN 104619328 A 5/2015
CN 106029066 A 10/2016
CN 107530435 A 1/2018
CN 104619328 B 10/2018
CN 106029066 B 3/2019
EP 0145121 A2 6/1985
EP 0375210 A1 6/1990
EP 375210 B1 5/1995
EP 1886695 A1 2/2008
EP 2306830 A4 6/2012
EP 2817019 A1 12/2014
EP 2817019 A4 4/2016
EP 3074011 A1 10/2016
EP 3111950 A1 1/2017
EP 2854814 B1 1/2018
EP 3074011 B1 7/2019
EP 3338781 B1 9/2019
HK 1208818 A 3/2016
HK 1228803 11/2017
HK 1230921 12/2017
HK 1208818 B 7/2018
IL 235868 A 4/2018
IN 10279/DELNP/2014 A 8/2016
IN 201617021323 A 8/2016
JP 322220 B1 4/1957
JP 04368384 A 12/1992
JP 09505030 A 5/1997
JP 2002506032 A 2/2002
JP 2002544271 A 12/2002
JP 2007528417 A 10/2007
JP 2008520606 A 6/2008

(56) References Cited

FOREIGN PATENT DOCUMENTS

| | | | |
|---|---|---|---|
| JP | 2014530812 | A | 11/2014 |
| JP | 2015517580 | A1 | 6/2015 |
| JP | 2016537394 | A | 12/2016 |
| JP | 6172871 | B | 7/2017 |
| JP | 2018012734 | A | 1/2018 |
| JP | 6516743 | B2 | 4/2019 |
| KR | 1020150021955 | A | 3/2015 |
| KR | 20160089506 | A | 7/2016 |
| KR | 102062640 | B1 | 1/2020 |
| MX | 365423 | B | 6/2019 |
| MX | 368167 | B | 9/2019 |
| MY | 172739 | A | 12/2019 |
| PE | 20542014 | A1 | 1/2015 |
| PE | 9466 | | 4/2019 |
| RU | 2381217 | C2 | 2/2010 |
| RU | 2009126745 | A | 1/2011 |
| RU | 2014151207 | A | 7/2016 |
| RU | 2014152625 | A | 7/2016 |
| RU | 2639867 | C2 | 12/2017 |
| RU | 2674983 | C1 | 12/2018 |
| SG | 11201604077 | W | 8/2019 |
| WO | 9410150 | A1 | 5/1994 |
| WO | 9504734 | A1 | 2/1995 |
| WO | 9945925 | A1 | 9/1999 |
| WO | 0069846 | A1 | 11/2000 |
| WO | 0180896 | A2 | 11/2001 |
| WO | 03015692 | A2 | 2/2003 |
| WO | 03061651 | A1 | 7/2003 |
| WO | 2004065351 | A1 | 8/2004 |
| WO | 2005087769 | A1 | 9/2005 |
| WO | 2008060391 | A2 | 5/2008 |
| WO | 2009050136 | A2 | 4/2009 |
| WO | 2009058944 | A2 | 5/2009 |
| WO | 2009064738 | A2 | 5/2009 |
| WO | 2010052445 | A1 | 5/2010 |
| WO | 2010132445 | A1 | 11/2010 |
| WO | 2010138758 | A1 | 12/2010 |
| WO | 2011113015 | A2 | 9/2011 |
| WO | 2011113015 | A3 | 10/2011 |
| WO | 2012027702 | A1 | 3/2012 |
| WO | 2012094618 | A1 | 7/2012 |
| WO | 2013039916 | A1 | 3/2013 |
| WO | 2013138371 | A1 | 9/2013 |
| WO | 2013177559 | A2 | 11/2013 |
| WO | 2013177559 | A3 | 1/2014 |
| WO | 2015061752 | A1 | 4/2015 |
| WO | 2015077414 | A1 | 5/2015 |
| WO | 2015077530 | A1 | 5/2015 |
| WO | 2015095811 | A2 | 6/2015 |
| WO | 2016014365 | A1 | 1/2016 |
| WO | 2016055533 | A1 | 4/2016 |
| WO | 2016141365 | A1 | 9/2016 |
| WO | 2016187347 | A1 | 11/2016 |
| WO | 2017023694 | A1 | 2/2017 |
| WO | 2017151613 | A1 | 9/2017 |
| WO | 2018049255 | A1 | 3/2018 |
| WO | 2020172501 | A1 | 8/2020 |
| WO | 2022031642 | A2 | 2/2022 |
| ZA | 201408182 | B | 9/2017 |

OTHER PUBLICATIONS

Munster et al., "Relacorilant (RELA) With Nab-paclitaxel (NP): Safety and Activity in Patients With Pancreatic Ductal Adenocarcinoma (PDAC) and Ovarian Cancer (OvCa)", Journal of Clinical Oncology , vol. 37, No. 15, May 1, 2019, 2 pages.

"A Guide to Drug Safety Terms at FDA", FDA Consumer Health Information, U.S. Food and Drug Administration, Available Online at: www.tinyurl.com/y6oao2sj, Nov. 2012, pp. 1-3.

"A Study of the Efficacy and Safety of CORLUX in the Treatment of Endogenous Cushing's Syndrome (SEISMIC)", U.S. National Library of Medicine, Accessed from Internet at Dec. 13, 2018, pp. 1-10.

"An Extension Study of CORLUX in the Treatment of Endogenous Cushing's Syndrome", Archive History for NCT00936741, U.S. National Library of Medicine, Jul. 9, 2009, pp. 1-7.

"Approval Letter", Center For Drug Evaluation and Research, Application No. 2021070rig1s000, Available Online at: http://www.accessdata.fda.gov/drugsatfda_docs/nda/2012/202107Orig1s000Approv.pdf, Feb. 17, 2017, pp. 1-7.

"BIAXIN (Clarithromycin)", May 2016, pp. 1-52.

"Case PGR2019-00048", Arguments Made by Petitioner in PGR2019-00048 and in the District Court Litigation, *Teva Pharmaceuticals USA, Inc.* v. *Corcept Therapeutics, Inc.*, U.S. Pat. No. 10,195,214, 2002, 2 pages.

"Case PGR2019-00048", Petitioner's Reply in Support of Petition for Post-Grant Review, *Teva Pharmaceuticals USA, Inc.* v. *Corcept Therapeutics, Inc.*, U.S. Pat. No. 10,195,214, Sep. 23, 2019, 6 pages.

"Case PGR2019-00048", Patent Owner's Authorized Sur-Reply in Further Support of Its Preliminary Response, *Teva Pharmaceuticals USA, Inc.* v. *Corcept Therapeutics, Inc.*, U.S. Pat. No. 10,195,214, Oct. 3, 2019, 7 pages.

"Case PGR2019-00048", Patent Owner's Exhibit List, *Teva Pharmaceuticals USA, Inc.* v. *Corcept Therapeutics, Inc.*, U.S. Pat. No. 10,195,214, Oct. 3, 2019, 7 pages.

"Case PGR2019-00048", Patent Owner Preliminary Response, *Teva Pharmaceuticals USA, Inc.* v. *Corcept Therapeutics, Inc*, U.S. Pat. No. 10,195,214, Aug. 23, 2019, 86 pages.

"Case PGR2019-00048", Petitioner's Exhibit List, *Teva Pharmaceuticals USA, Inc.* v. *Corcept Therapeutics, Inc.*, U.S. Pat. No. 10,195,214, Sep. 23, 2019, 9 pages.

"Case PGR2019-00048", Opinion, *Teva Pharmaceuticals USA, Inc.* v. *Corcept Therapeutics, Inc.*, Corcept Ex. 2004, Oct. 23, 2018, pp. 1-7.

"Certification and Request for Prioritized Examination Under 37 CFR 1.102(e)", Doc Code: TRACK1.REQ, Document Description: TrackOne RequestTEVA1035, pt. 1, Jun. 19, 2017, 428 pages.

"Clinical Drug Interaction Studies—Study Design, Data Analysis, and Clinical Implications Guidance for Industry", U.S. Department of Health and Human Services Food and Drug Administration Center for Drug Evaluation and Research, Oct. 2017, 32 pages.

"Clinical Pharmacology and Biopharmaceutics Review(s)", Center For Drug Evaluation and Research, Application No. 202107Orig1s000, Available Online at: http://www.accessdata.fda.gov/drugsatfda_docs/nda/2012/2021070rig1 s000ClinPharmR.pdf, Feb. 18, 2017, pp. 1-120.

"Concomitant Administration of Glucocorticoid Receptor Modulators and CYP3A Inhibitors", Petition for Post- Grant Review Under 35 U.S.C. §§ 321-328 and 37 C.F.R. § 42.200 et seq., Case No. PGR2019-00048, U.S. Pat. No. 10,195,214, May 7, 2019, 78 pages.

"Corcept Therapeutics Incorporated Announces FDA Approval of Korlym(™) (Mifepristone): First and Only Approved Medication for Cushing's Syndrome Patients", Corcept Therapeutics Press Release, Available Online at: https://www.sec.gov/Archives/edgar/data/1088856/000119312512347804/d357533d10q.htm, Accessed from Internet on Apr. 25, 2019, 5 pages.

"CRIXIVAN (Indinavir Sulfate)", Merck & Co., Inc., Sep. 2016, pp. 1-29.

"Cross Discipline Team Leader Review", Center for Drug Evaluation and Research, Application No. 202107Orig1s000, *Teva Pharmaceuticals USA, Inc.* v. *Corcept Therapeutics, Inc.*, PGR2019-00048, Corcept Ex. 2055, Feb. 13, 2012, pp. 1-32.

"Decision", Case PGR2019-00048, Nov. 20, 2019, pp. 1-37.

"Declaration of F. Peter Guengerich, Ph.D.", Case PGR2019-00048, *Teva Pharmaceuticals USA, Inc.* v. *Corcept Therapeutics, Inc.*, Corcept Ex. 2056, 2019, 232 pages.

"Declaration of J.C. Rozendaal in Support of Petitioner's Motion for Pro Hac Vice Admission", Case PGR2019-00048, Sep. 11, 2019, 6 pages.

"Declaration of Laurence Katznelson, M.D.", Case PGR2019-00048, *Teva Pharmaceuticals USA, Inc.* v. *Corcept Therapeutics, Inc.*, Corcept Ex. 2058, 2019, 83 pages.

"Declaration of Nicholas A. Locastro", Case PGR2019-00048 , *Teva Pharmaceuticals USA, Inc.* v. *Corcept Therapeutics, Inc.*, Corcept Ex. 2048, Dec. 17, 2019, pp. 1-3.

(56) References Cited

OTHER PUBLICATIONS

"Declaration of Ty Carroll, M.D.", Case PGR2019-00048, *Teva Pharmaceuticals USA, Inc.* v. *Corcept Therapeutics, Inc.*, Corcept Ex. 2057, 2019, 59 pages.
"Declaration of Uma N. Everett in Support of Petitioner's Motion for Pro Hac Vice Admission", Case PGR2019-00048, Sep. 11, 2019, 5 pages.
"Declaration of William H. Milliken in Support of Petitioner's Motion for Pro Hac Vice Admission", Case PGR2019-00048, Teva1062, Sep. 11, 2019, 6 pages.
"Defendant Teva Pharmaceuticals USA, Inc.'s Preliminary Invalidity Contentions", *Corcept Therapeutics, Inc.*, Plaintiff, v. *Teva Pharmaceuticals USA, Inc.*, Civil Action No. 2:18-cv-03632 (SDW)(CLW) (Consolidated), May 13, 2019, 138 pages.
"Drug Development and Drug Interactions: Table of Substrates, Inhibitors and Inducers", FDA website (cached), Available Online at: https://www.fda.gov/Drugs/DevelopmentApprovaiProcess/DevelopmentResources/DrugInteractionslabeling/ucm093664.html, Dec. 8, 2017, pp. 1-16.
"Drugs@FDA: FDA Approved Drug Products", Available Online at: https://www.accessdata.fda.gov/scripts/cder/daf/, Accessed from Internet at May 6, 2019, pp. 1-3.
"European Medicines Agency Recommends Suspension of Marketing Authorisations for Oral Ketoconazole", European Medicines Agency, Jul. 26, 2013, pp. 1-3.
"Excerpts of Physician's Desk Reference", 58th Edition, 2004, pp. 1-3.
"FDA Advises Against Using Oral Ketoconazole in Drug Interaction Studies Due to Serious Potential Side Effects", Drugs, Home Drugs, Drug Safety and Availability, Available Online at: http://www.fda.gov/Drugs/DrugSafety/ucm371017.htm, Accessed from Internet on Feb. 11, 2020, pp. 1-2.
"FDA Guidance Documents", Regulatory Information, Available Online at: https://www.fda.gov/regulatoryinformation/guidances/, Accessed from Internet at May 6, 2019, pp. 1-3.
"FDA Label for KORLYM®", Available Online at: https://www.accessdata.fda.gov/drugsatfda_docs/label/2012/202107s000lbl.pdf, Oct. 25, 2016, 23 pages.
"File History for U.S. Pat. No. 9,943,526", Optimizing Mifepristone Levels for Cushing's Patients, Apr. 17, 2018, 257 pages.
"Food and Drug Administration Approval Letter for Korlym (Mifepristone) Tablets", NDA 20217, Feb. 17, 2012, pp. 1-6.
"Food-Effect Bioavailability and Fed Bioequivalence Studies", FDA Guidance for Industry, U.S. Department of Health and Human Services Food and Drug Administration Center for Drug Evaluation and Research (CDER), Dec. 2002, pp. 1-12.
"Form 10-Q", Available Online at: https://www.sec.gov/Archives/edgar/data/1088856/000110262412000138/corcept-therapeuticsincorpora.htm, Jun. 30, 2012, pp. 1-76.
"Form 8-K Current Report", Corcept Therapeutics Incorporated, Available Online at: https://www.sec.gov/Archives/edgar/data/1088856/000110262412000138/corcepttherapeutics8k.htm, Feb. 17, 2012, pp. 1-2.
"Guidance for Industry—Drug Interaction Studies—Study Design, Data Analysis, and Implications for Dosing and Labeling", Draft Guidance, Clinical Pharmacology, TEVA1052, Sep. 2006, 55 pages.
"Hyperglycemia in Diabetes", The Mayo Clinic, Available Online at: https://www.mayoclinic.org/diseasesconditions/hyperglycemia/symptoms-causes/syc-20373631, Nov. 3, 2018, 6 pages.
"Incivek (Telaprevir)", *Teva Pharmaceuticals USA, Inc.* v. *Corcept Therapeutics, Inc.*, Oct. 2013, pp. 1-28.
"Invirase (Saquinavir Mesylate)", *Teva Pharmaceuticals USA, Inc.* v. *Corcept Therapeutics, Inc.*, Sep. 2016, pp. 1-31.
"Kaletra (Lopinavir and Ritonavir)", *Teva Pharmaceuticals USA, Inc.* v. *Corcept Therapeutics, Inc.*, Nov. 2016, pp. 1-64.
"Korlym (Mifepristone) Tablets", Drug Approval Package, Application No. 202107, Available Online at: www.accessdata.fda.gov/drugsatfda_docs/nda/2012/202107_korlym toc.cfm], Accessed from Internet at May 7, 2019, pp. 1-2.
"Korlym Label", Available Online at: https://web.archive.org/web/20120304133653/www.corcept.com/prescribinginfo.pdf, Mar. 4, 2012, pp. 1-17.
"Korlym Label Revised", May 2017, pp. 1-7.
"Korlym™ (Mifepristone) 300 mg Tablets", Reference ID: 3089791, TEVA1004, Feb. 17, 2012, pp. 1-23.
"Labeling", Korlym™ ((mifepristone) [package insert]; Center for Drug Evaluation and Research, Corcept Therapeutics, Inc., Feb. 2012, 26 pages.
"Letter Order", Case PGR2019-00048, *Teva Pharmaceuticals USA, Inc.* v. *Corcept Therapeutics, Inc.*, Corcept Ex. 2005, Jun. 4, 2019, pp. 1-2.
"Medical Encyclopedia", Medline Plus, Available Online at: http://www.nlm.nih.gov/medlineplus/ency/article/003430.htm, Oct. 2005, pp. 1-4.
"National Court-Reporting Coverage", *Teva Pharmaceuticals USA, Inc.* v. *Corcept Therapeutics, Inc.*, PGR2019-00048 Corcept Ex. 2059, Feb. 14, 2020, pp. 1-81.
"Nefazodone Hydrochloride Tablets", *Teva Pharmaceuticals USA, Inc.* v. *Corcept Therapeutics, Inc.*, May 2014, pp. 1-4.
"Nizoral (ketoconazole)", Janssen Pharmaceuticals, Jul. 2013, pp. 1-22.
"Norvir (Ritonavir)", Full Prescribing Information, *Teva Pharmaceuticals USA, Inc.* v. *Corcept Therapeutics, Inc.*, Dec. 2016, pp. 1-42.
"Notice Concerning Alternative Dispute Resolution", Case PGR2019-00048, May 24, 2019, pp. 1-6.
"Notice of Accepting Corrected Exhibit", Case PGR2019-00048, May 30, 2019, 2 pages.
"Notice of Deposition of Dr. David J. Greenblatt, M.D.", Case PGR2019-00048, Jan. 17, 2020, 4 pages.
"Notice of Joint Stipulation to Modify Trial Due Dates 1, 2 and 3", Case PGR2019-00048, Jan. 6, 2020, 4 pages.
"Noxafil (Posaconazole)", Full Prescribing Information, *Teva Pharmaceuticals USA, Inc.* v. *Corcept Therapeutics, Inc.*, Sep. 2016, pp. 1-37.
"Objections to Evidence", Case PGR2019-00048, Teva Pharmaceuticals USA, Inc.'s, Mar. 5, 2020, 5 pages.
"Order", Case PGR2019-00048, Oct. 3, 2019, pp. 1-3.
"Order", Case PGR2019-00048, Paper 24, Nov. 20, 2019, pp. 1-5.
"Order, Paper 22", Case PGR2019-00048, Nov. 20, 2019, 5 pages.
"Order, Paper 23", Case PGR2019-00048, Nov. 20, 2019, pp. 1-5.
"Patent Owner Mandatory Notices", Case PGR2019-00048, May 28, 2019, 5 pages.
"Patent Owner Response", Case PGR2019-00048, Feb. 27, 2020, 92 pages.
"Patent Owner's Objections to Evidence", Case PGR2019-00048, Dec. 5, 2019, 5 pages.
"Petitioner's Motion for Pro Hac Vice Admission of J.C. Rozendaal Under 37 C.F.R. § 42.10(C)", Case PGR2019-00048, Sep. 11, 2019, pp. 1-8.
"Petitioner's Motion for Pro Hac Vice Admission of Uma N. Everett Under 37 C.F.R. § 42.10(C)", Case PGR2019-00048, Sep. 11, 2019, pp. 1-7.
"Petitioner's Motion for Pro Hac Vice Admission of William H. Milliken Under 37 C.F.R. § 42.10(C)", Case PGR2019-00048, Sep. 11, 2019, pp. 1-8.
"Power of Attorney", Case PGR2019-00048, Teva Pharmaceuticals USA, Inc.'s, May 7, 2019, 3 pages.
"Power of Attorney for Proceedings Before the Patent Trial and Appeal Board", May 28, 2019, 1 page.
"Pretrial Scheduling Order", Civil Action No. 18-3632 (SDW)(CLW), United States District Court, District of New Jersey, Feb. 11, 2019, pp. 1-3.
"Scheduling Order, Paper 20", Case PGR2019-00048, Nov. 20, 2019, pp. 1-5.
"Sporanox (Itraconazole)", Apr. 2015, 71 pages.
"Technivie (Ombitasvir, Paritaprevir and Ritonavir)", Feb. 2017, pp. 1-35.
"The Hazards of Seldane", The New York Times, Jan. 17, 1997, pp. 1-2.
"Transmittal Letter Accompanying Submission of Replacement Exhibit 1056", Case PGR2019-00048, May 28, 2019, 3 pages.

(56) References Cited

OTHER PUBLICATIONS

"Treatment for Aspergillosis", Centers for Disease Control and Prevention, Available Online at: https://www.cdc.gov/fungal/diseases/aspergillosis/treatment.html, Jan. 2, 2019, 1 page.
"Trial Practice Guide Update", *Teva Pharmaceuticals USA, Inc.* v. *Corcept Therapeutics, Inc.*, PGR2019-00048 Corcept Ex. 2001, Aug. 2018, pp. 1-31.
"Tybost (Cobicistat)", Jun. 2016, pp. 1-32.
"Updated Mandatory Notices", Case PGR2019-00048, Teva Pharmaceuticals USA, Inc.'s, Sep. 11, 2019, 3 pages.
"Vaprisol (Conivaptan Hydrochloride)", Oct. 2016, pp. 1-14.
"Vfend (Voriconazole)", Feb. 2013, pp. 1-42.
"Victrelis (Boceprevir)", Jan. 2017, pp. 1-38.
"Viracept (Nelfinavir Mesylate)", Sep. 2016, pp. 1-28.
U.S. Appl. No. 15/627,359 , Final Office Action, Mailed On Jun. 12, 2018, 13 pages.
U.S. Appl. No. 15/627,359 , Non-Final Office Action, Mailed On Oct. 20, 2017, 11 pages.
U.S. Appl. No. 15/627,359 , Notice of Allowance, Mailed On Dec. 12, 2018, 10 pages.
U.S. Appl. No. 15/627,359 , "Preliminary Invalidity Contentions", Defendant Teva Pharmaceuticals, Corcept Therapeutics, Civil Action No. 2: 18-cv-03632, May 13, 2019, 143 pages.
U.S. Appl. No. 15/627,359 , "Rule 132 Declaration by Dr. Hanford K.S. Yau and CV", Jun. 28, 2018, 27 pages.
U.S. Appl. No. 15/627,359 , "Rule 132 Declaration by Dr. Paul G. Pearson and CV", Jun. 28, 2018, 36 pages.
U.S. Appl. No. 15/627,359 , "Rule 132 Declaration of Dr. Andreas Moraitis and CV", Jun. 28, 2018, 32 pages.
U.S. Appl. No. 15/627,359 , "Rule 132, Declaration of Joseph K. Belanoff and CV", Dec. 15, 2017, 15 pages.
U.S. Appl. No. 15/627,368 , Advisory Action, Mailed On Feb. 20, 2018, 3 pages.
U.S. Appl. No. 15/627,368 , Advisory Action, Mailed On Mar. 2, 2018, 3 pages.
U.S. Appl. No. 15/627,368 , Final Office Action, Mailed On Dec. 5, 2017, 10 pages.
U.S. Appl. No. 15/627,368 , Final Office Action, Mailed On Jul. 5, 2019, 10 pages.
U.S. Appl. No. 15/627,368 , Final Office Action, Mailed On Oct. 22, 2018, 8 pages.
U.S. Appl. No. 15/627,368 , Non-Final Office Action, Mailed On Aug. 8, 2017, 11 pages.
U.S. Appl. No. 15/627,368 , Non-Final Office Action, Mailed On Mar. 16, 2018, 13 pages.
U.S. Appl. No. 15/627,368 , Non-Final Office Action, Mailed On Dec. 17, 2018, 14 pages.
U.S. Appl. No. 16/219,564 , Non-Final Office Action, Mailed On Jan. 10, 2020, 11 pages.
U.S. Appl. No. 16/219,564, Notice of Allowance, Mailed On Oct. 19, 2020, 5 pages.
U.S. Appl. No. 17/331,130 , Final Office Action, Mailed On Dec. 10, 2021, 11 pages.
U.S. Appl. No. 17/331,130 , Non-Final Office Action, Mailed On Aug. 9, 2021, 17 pages.
U.S. Appl. No. 17/331,130 , Notice of Allowance, Mailed On Jan. 5, 2022, 10 pages.
U.S. Appl. No. 17/672,380 , Final Office Action, Mailed On Jan. 9, 2024, 14 pages.
U.S. Appl. No. 17/672,380 , Non-Final Office Action, Mailed On Jul. 18, 2023, 36 pages.
U.S. Appl. No. 17/672,380 , Notice of Allowance, Mailed On Feb. 14, 2024, 6 pages.
Aanderud et al., "Plasma Cortisol Concentrations After Oral Substitution of Cortisone in the Fasting and Non-Fasting State", Acta Medica Scandinavica, vol. 210, No. 3, Jan.-Dec. 1981, pp. 157-161.
Albertson et al., "Effect of the Antiglucocorticoid RU486 on Adrenal Steroidogenic Enzyme Activity and Steroidogenesis", European Journal of Endocrinology, vol. 130, No. 2, Feb. 1994, pp. 195-200.
Ansaloni et al., "Pharmacokinetics of Concomitant Cisplatin and Paclitaxel Administered by Hyperthermic Intraperitoneal Chemotherapy to Patients with Peritoneal Carcinomatosis from Epithelial Ovarian Cancer", British Journal of Cancer, vol. 112, Issue 2, 2015, pp. 306-312.
Asser et al., "Autocrine Positive Regulatory Feedback of Glucocorticoid Secretion: Glucocorticoid Receptor Directly Impacts H295R Human Adrenocortical Cell Function", Molecular and Cellular Endocrinology, vol. 395, Nos. 1-2, Sep. 2014, pp. 1-9.
Bagchus et al., "Important Effect of Food on the Bioavailability of Oral Testosterone Undecanoate", Pharmacotherapy, vol. 23, No. 3, Mar. 2003, pp. 319-325.
Bailey et al., "Grapefruit-Medication Interactions: Forbidden Fruit or Avoidable Consequences?", Canadian Medical Association Journal, vol. 185, No. 4, Mar. 5, 2013, pp. 309-316.
Banankhah et al., "Ketoconazole-Associated Liver Injury in Drug-Drug Interaction Studies in Healthy Volunteers", The Journal of Clinical Pharmacology, vol. 56, No. 10, Oct. 2016, pp. 1196-1202.
Basina et al., "Successful Long-Term Treatment of Cushing Disease with Mifepristone (RU 486)", Endocrine Practice, vol. 18, No. 5, Sep.-Oct. 2012, 7 pages.
Belanoff et al., "An Open Label Trial of C-1073 (Mifepristone) for Psychotic Major Depression", Biological Psychiatry, vol. 52, No. 5, Sep. 1, 2002, pp. 386-392.
Benagiano et al., "Selective Progesterone Receptor Modulators 3: Use in Oncology, Endocrinology and Psychiatry", Expert Opinion Pharmacotherapy, vol. 9, No. 14, Oct. 2008, pp. 2487-2496.
Benet et al., "Pharmacokinetics: The Dynamics of Drug Absorption, Distribution and Elimination", Chapter 1, Goodman & Gilman's: The Pharmacological Basis of Therapeutics, Eighth Edition, 1990, pp. 3-32.
Bertagna et al., "Chapter 16: Cushing's Disease", The Pituitary (Shlomo Melmed, 3rd Edition), Part 1, 2011, pp. 533-577.
Bertagna et al., "Chapter 16: Cushing's Disease", The Pituitary (Shlomo Melmed, 3rd Edition), Part 2, 2011, pp. 578-617.
Bertagna et al., "Pituitary-Adrenal Response to the Antiglucocorticoid Action of RU 486 in Cushing's Syndrome", Journal of Clinical Endocrinology and Metabolism, vol. 63, No. 3, Sep. 1986, pp. 639-643.
Berthois et al., "A Multiparametric Analysis of Endometrial Estrogen and Progesterone Receptors After the Postovulatory Administration of Mifepristone", Fertility and Sterility, vol. 55, No. 3, Mar. 1991, pp. 547-554.
Blasey et al., "Efficacy and Safety of Mifepristone for the Treatment of Psychotic Depression", Journal of Clinical Psychopharmacology, vol. 31, No. 4, Aug. 2011, pp. 436-440.
Brogden et al., "Mifepristone: A Review of its Pharmacodynamic and Pharmacokinetic Properties, and Therapeutic Potential", Drugs, vol. 45, No. 3, Mar. 1993, pp. 384-409.
Carroll et al., "The Use of Mifepristone in the Treatment of Cushing's Syndrome", Drugs of Today, vol. 48, No. 8, Aug. 2012, pp. 509-518.
Cassier et al., "Mifepristone for Ectopic ACTH Secretion in Metastic Endocrine Carcinomas: Report of Two Cases", European Journal of Endocrinology, vol. 158, No. 6, Jun. 2008, pp. 935-938.
Castinetti et al., "Ketoconazole in Cushing's Disease: Is It Worth a Try?", The Journal of Clinical Endocrinology & Metabolism, vol. 99, No. 5, May 2014, pp. 1623-1630.
Castinetti et al., "Medical Treatment of Cushing's Syndrome: Glucocorticoid Receptor Antagonists and Mifepristone", Neuroendocrinology, vol. 92, 2010, pp. 125-130.
Castinetti et al., "Merits and Pitfalls of Mifepristone in Cushing's Syndrome", European Journal of Endocrinology, vol. 160, No. 6, Jun. 2009, pp. 1003-1010.
Charmandari et al., "Adrenal Insufficiency", Lancet, vol. 383, No. 9935, Available Online at: https://www.thelancet.com/journals/lancet/article/PIIS0140-6736(13)61684-0/fulltext, Feb. 4, 2014, pp. 1-16.
Chrousos et al., "Glucocorticoids and Glucocorticoid Antagonists: Lessons from RU 486", Antiglucocorticoids, Kidney International, vol. 34, Oct. 1988, pp. S-18-S-23.

(56) References Cited

OTHER PUBLICATIONS

Clayton et al., "Mortality in Patients with Cushing's Disease More Than 10 Years After Remission: A Multicentre, Multinational, Retrospective Cohort Study", Lancet Diabetes Endocrinology, vol. 4, No. 7, Jul. 2016, pp. 569-576.
Cuevas-Ramos et al., "Treatment of Cushing's Disease: A Mechanistic Update", Journal of Endocrinology, vol. 223, No. 2, Nov. 2014, pp. R19-R39.
Cuevas-Ramos et al., "Update on Medical Treatment for Cushing's Disease", Clinical Diabetes and Endocrinology, vol. 2, No. 16, Sep. 13, 2016, pp. 1-13.
Cuneo et al., "Metyrapone Pre-Treated Inferior Petrosal Sinus Sampling in the Differential Diagnosis of ACTH-Dependent Cushing's Syndrome", Clinical Endocrinology, vol. 46, No. 5, May 1997, pp. 607-618.
Dang et al., "Pharmacological Management of Cushing's Syndrome: An Update", Arq Bras Endocrinol Metab, vol. 51, No. 8, Nov. 2007, pp. 1339-1348.
Davis et al., "Guidelines for Counselling Patients Receiving Drugs Used in the Treatment of Neoplastic Disease: A Pharmacist's Guide to Advisory Labels and Patient Information", The Australian Journal of Hospital Pharmacy, vol. 31, No. 1, Mar. 2001, pp. 51-55.
De Lignieres , "Oral Micronized Progesterone", Clinical Therapeutics, vol. 21, No. 1, Jan. 1999, pp. 41-60.
Dunnigan et al., "Mifepristone (RU-486) in the Treatment of Refractory Cushing's Disease", Endocrine Reviews, vol. 31, No. 3, Jun. 2010, 9 pages.
Ehrenkranz et al., "SUN-66: Using Mifepristone to Differentiate Cushing's Disease From Cushing's Syndrome", The Endocrine Society's 95th Annual Meeting and Expo, Jun. 15-18, 2013, 6 pages.
El-Shafie et al., "Adrenocorticotropic Hormone-Dependent Cushing's Syndrome: Use of an Octreotide Trial to Distinguish Between Pituitary or Ectopic Sources", Sultan Qaboos University Medical Journal, vol. 15, No. 1, Feb. 2015, pp. 120-123.
Feelders et al., "The Burden of Cushing's Disease: Clinical and Health-Related Quality of Life Aspects", European Journal of Endocrinology, vol. 167, No. 3, Sep. 2012, pp. 311-326.
Fein et al., "Sustained Weight Loss in Patients Treated with Mifepristone for Cushing's Syndrome: A Follow-Up Analysis of the SEISMIC Study and Long-Term Extension", BMC Endocrine Disorders, vol. 15, No. 63, Oct. 27, 2015, 7 pages.
Fleseriu et al., "A New Therapeutic Approach in the Medical Treatment of Cushing's Syndrome: Glucocorticoid Receptor Blockade with Mifepristone", Endocrine Practice, vol. 19, No. 2, Mar. 1, 2013, pp. 313-326.
Fleseriu et al., "Changes in Plasma ACTH Levels and Corticotroph Tumor Size in Patients with Cushing's Disease During Long-Term Treatment with the Glucocorticoid Receptor Antagonist Mifepristone", Journal of Clinical Endocrinology Metabolism, vol. 99, No. 10, Oct. 2014, pp. 3718-3727.
Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, No. 6, Mar. 30, 2012, pp. 2039-2049.
Fleseriu et al., "New Avenues in the Medical Treatment of Cushing's Disease: Corticotroph Tumor Targeted Therapy", Journal of Neuro-Oncology, vol. 114, No. 1, Aug. 2013, pp. 1-11.
Friedman et al., "Rational Therapeutic Drug Monitoring", JAMA, vol. 256, No. 16, Oct. 24-31, 1986, pp. 2227-2233.
Gal et al., "Effect of Ketoconazole on Steroidogenic Human Granulosa-Luteal Cells in Culture", European Journal of Obstetrics & Gynecology and Reproductive Biology, vol. 39, No. 3, May 10, 1991, pp. 209-214.
Gallagher et al., "Mifepristone (RU-486) Treatment for Depression and Psychosis: A Review of the Therapeutic Implications", Neuropsychiatric Disease and Treatment, vol. 2, No. 1, Mar. 2006, pp. 33-42.
Greenblatt , "Clinical Pharmacokinetics", The New England Journal of Medicine, vol. 293, No. 14, Oct. 2, 1975, pp. 702-705.
Greenblatt et al., "Clinical Studies of Drug-Drug Interactions: Design and Interpretation", Springer, 2010, pp. 625-649.
Greenblatt , "Concomitant Administration of Glucocorticoid Receptor Modulators and CYP3A Inhibitors", Petition for Post-Grant Review, U.S. Pat. No. 10,195,214, TEVA1002- Declaration of Dr. David J. Greenblatt, M.D., May 7, 2019, 118 pages.
Greenblatt , "Curriculum Vitae", TEVA 1003, Apr. 2019, 83 pages.
Greenblatt , "Drug-Drug Noninteractions", Cardiovascular Therapeutics, vol. 27, No. 4, 2009, pp. 226-229.
Greenblatt , "In Vitro Prediction of Clinical Drug Interactions with CYP3A Substrates: We Are Not There Yet", Clinical Pharmacology & Therapeutics, vol. 95, No. 2, Feb. 2014, pp. 133-135.
Greenblatt et al., "Ketoconazole Inhibition of Triazolam and Alprazolam Clearance: Differential Kinetic and Dynamic Consequences", Clinical Pharmacology and Therapeutics, vol. 64, No. 3, Sep. 1998, pp. 237-247.
Greenblatt et al., "Kinetic and Dynamic Interaction Study of Zolpidem with Ketoconazole, Itraconazole and Fluconazole", Clinical Pharmacology & Therapeutics, vol. 64, No. 6, Dec. 1998, pp. 661-671.
Greenblatt et al., "Liver Injury Associated with Ketoconazole: Review of the Published Evidence", The Journal of Clinical Pharmacology, vol. 54, No. 12, Dec. 2014, pp. 1321-1329.
Greenblatt et al., "Mechanism of Cytochrome P450-3A Inhibition by Ketoconazole", Journal of Pharmacy and Pharmacology, vol. 63, No. 2, Feb. 2011, pp. 214-221.
Greenblatt et al., "Pharmacokinetics and Pharmacodynamics for Medical Students: A Proposed Course Outline", The Journal of Clinical Pharmacology, vol. 56, No. 10, Oct. 2016, pp. 1180-1195.
Greenblatt et al., "Ritonavir is the Best Alternative to Ketoconazole as an Index Inhibitor of Cytochrome P450-3A in Drug-Drug Interaction Studies", British Journal of Clinical Pharmacology, vol. 80, No. 3, Sep. 2015, pp. 342-350.
Greenblatt et al., "The CYP3 Family", Cytochromes P450: Role in the Metabolism and Toxicity of Drugs and Other Xenobiotics, Royal Society of Chemistry, Chapter 11, Jan. 2008, pp. 354-383.
Gross et al., "Mifepristone Reduces Weight Gain and Improves Metabolic Abnormalities Associated with Risperidone Treatment in Normal Men", Obesity, vol. 18, No. 12, Dec. 2010, pp. 2295-2300.
Guelho et al., "Emerging Drugs for Cushing's Disease", Expert Opinion on Emerging Drugs, vol. 20, No. 3, Sep. 2015, pp. 463-478.
Healy et al., "Pituitary and Adrenal Responses to the Anti-Progesterone and Anti-Glucocorticoid Steroid RU 486 in Primates", Journal of Clinical Endocrinology and Metabolism, vol. 57, No. 4, Oct. 1983, pp. 863-865.
Heikinheimo et al., "Antiprogesterone RU 486—A Drug for Non-Surgical Abortion", Annals of Medicine, vol. 22, No. 2, Apr. 1990, pp. 75-84.
Heikinheimo , "Clinical Pharmacokinetics of Mifepristone", Clinical Pharmacokinetics, vol. 33, No. 1, Jul. 1997, pp. 7-17.
Heikinheimo , "Pharmacokinetics of the Antiprogesterone RU 486 in Women During Multiple Dose Administration", The Journal of Steroid Biochemistry and Molecular Biology, vol. 32, No. 1A, Jan. 1989, pp. 21-25.
Heikinheimo et al., "The Pharmacokinetics of Mifepristone in Humans Reveal Insights Into Differential Mechanisms of Antiprogestin Action", Contraception, vol. 68, No. 6, Dec. 2003, pp. 421-426.
Huang et al., "Pharmacokinetics and Dose Proportionality of Ketoconazole in Normal Volunteers", Antimicrobial Agents and Chemotherapy, vol. 30, No. 2, Aug. 1986, pp. 206-210.
Im et al., "Mifepristone: Pharmacology and Clinical Impact in Reproductive Medicine, Endocrinology and Oncology", Expert Opinion on Pharmacotherapy, Drug Evaluation, vol. 11, No. 3, Feb. 2010, pp. 481-488.
Isokangas et al., "Paclitaxel (Taxol) and Carboplatin Followed by Concomitant Paclitaxel, Cisplatin and Radiotherapy for Inoperable Stage III NSCLC", Lung Cancer, vol. 20, Issue 2, May 1, 1998, pp. 127-133.
Jang et al., "Identification of CYP3A4 as the Principal Enzyme Catalyzing Mifepristone (RU 486) Oxidation in Human Liver Microsomes", Biochem. Pharmacol., vol. 52, No. 5, Sep. 13, 1996, pp. 753-761.

(56) References Cited

OTHER PUBLICATIONS

Johanssen et al., "Mifepristone (RU 486) in Cushing's Syndrome", European Journal of Endocrinology, vol. 157, No. 5, Nov. 2007, pp. 561-569.
Kaeser et al., "Drug-Drug Interaction Study of Ketoconazole and Ritonavir-Boosted Saquinavir", Antimicrobial Agents and Chemotherapy, vol. 53, No. 2, Feb. 2009, pp. 609-614.
Kaushik et al., "Concomitant Administration of Glucocorticoid Receptor Modulators and CYP3A Inhibitors", Petition for Post-Grant Review, U.S. Pat. No. 10,195,214, Declaration of Atul Kaushik, May 7, 2019, 5 pages.
Ke et al., "Itraconazole and Clarithromycin as Ketoconazole Alternatives for Clinical CYP3A Inhibition Studies", Clinical Pharmacology & Therapeutics, vol. 95, No. 5, May 2014, pp. 473-476.
Kumar et al., "Cytochrome P450-Mediated Metabolism of the HIV-1 Protease Inhibitor Ritonavir (ABT-538) in Human Liver Microsomes", The Journal of Pharmacology and Experimental Therapeutics, vol. 277, No. 1, Apr. 1996, pp. 423-431.
Latrille et al., "A Comparative Study of the Effects of Ketoconazole and Fluconazole on 17-B Estradiol Production by Rat Ovaries in Vitro", Research Communications in Chemical Pathology and Pharmacology, vol. 64, No. 1, Apr. 1989, pp. 173-177.
Lee et al., "Office of Clinical Pharmacology Review Memorandum", NDA 20687, Addendum, Korlym ™ Mifepristone, Jan. 13, 2012, 119 pages.
Lindberg , "Emergency Contraception: The Nurse's Role in Providing Postcoital Options", Journal of Obstetric, Gynecologic, & Neonatal Nursing, vol. 26, No. 2, Mar.-Apr. 1997, pp. 145-152.
Locniskar et al., "Interaction of Diazepam with Famotidine and Cimetidine, Two H2-Receptor Antagonists", The Journal of Clinical Pharmacology, vol. 26, No. 4, Apr. 1986, pp. 299-303.
Luft , "Novel Cell Therapy for Type 1 Diabetes Mellitus", Journal of Molecular Medicine, vol. 87, May 9, 2009, pp. 659-661.
Molitch , "Current Approaches to the Pharmacological Management of Cushing's Disease", Molecular and Cellular Endocrinology, vol. 408, Jun. 15, 2015, pp. 185-189.
Moncet et al., "Ketoconazole Therapy: An Efficacious Alternative to Achieve Eucortisolism in Patients with Cushing's Syndrome", Medicina (B Aires), vol. 67, No. 1, 2007, pp. 26-31.
Morgan et al., "Mifepristone for Management of Cushing's Syndrome", Pharmacotherapy, vol. 33, No. 3, 2013, pp. 319-329.
Nguyen et al., "Effects of Ketoconazole on the Pharmacokinetics of Mifepristone, a Competitive Glucocorticoid Receptor Antagonist, in Healthy Men", Advances in Therapy, vol. 34, No. 10, Oct. 2017, pp. 2371-2385.
Nieman et al., "Successful Treatment of Cushing's Syndrome with the Glucocorticoid Antagonist RU 486", Journal of Clinical Endocrinology Metabolism, vol. 61, No. 3, Sep. 1985, pp. 536-540.
Ohno et al., "General Framework for the Quantitative Prediction of CYP3A4-Mediated Oral Drug Interactions Based on the AUC Increase by Coadministration of Standard Drugs", Clinical Pharmacokinetics, vol. 46, No. 8, 2007, pp. 681-696.
Oosterhuis et al., "Life-Threatening Pneumocystis Jiroveci Pneumonia Following Treatment of Severe Cushing's Syndrome", The Netherlands Journal of Medicine, vol. 65, No. 6, Jun. 2007, pp. 215-217.
Outeiro et al., "No Increased Risk of Ketoconazole Toxicity in Drug-Drug Interaction Studies", The Journal of Clinical Pharmacology, vol. 56, No. 10, Oct. 2016, pp. 1203-1211.
Para et al., "Phase I/II Trial of the Anti-HIV Activity of Mifepristone in HIV-Infected Subjects ACTG 5200", Journal of Acquired Immune Deficiency Syndromes, vol. 53, No. 4, Apr. 1, 2010, pp. 491-495.
International Patent Application No. PCT/EP2008/063699 , International Search Report and Written Opinion, Mailed On May 6, 2009, 12 pages.
International Patent Application No. PCT/US2017/013974 , International Search Report and Written Opinion, Mailed On Apr. 20, 2017, 12 pages.
International Patent Application No. PCT/US2018/020336 , International Preliminary Report on Patentability, Mailed On Sep. 12, 2019, 9 pages.
International Patent Application No. PCT/US2018/020336 , International Search Report and Written Opinion, Mailed On May 15, 2018, 11 pages.
International Patent Application No. PCT/US2021/034332 , International Preliminary Report on Patentability, Mailed On Dec. 8, 2022, 5 pages.
International Patent Application No. PCT/US2021/034332 , International Search Report and Written Opinion, Mailed On Sep. 9, 2021, 9 pages.
Pivonello et al., "The Treatment of Cushing's Disease", Endocrine Reviews, vol. 36, No. 4, Aug. 2015, pp. 385-486.
Pozza et al., "Management Strategies for Aggressive Cushing's Syndrome: From Macroadenomas to Ectopics", Journal of Oncology, vol. 2012, Aug. 9, 2012, pp. 1-9.
Reimondo et al., "The Corticotrophin-Releasing Hormone Test is the Most Reliable Noninvasive Method to Differentiate Pituitary from Ectopic ACTH Secretion in Cushing's Syndrome", Clinical Endocrinology, vol. 58, No. 6, Jun. 2003, pp. 718-724.
Ritzel et al., "ACTH After 15 Min Distinguishes Between Cushing's Disease and Ectopic Cushing's Syndrome: A Proposal for a Short and Simple CRH Test", European Journal of Endocrinology, vol. 173, No. 2, Aug. 2015, pp. 197-204.
Saav et al., "Medical Abortion in Lactating Women—Low Levels of Mifepristone in Breast Milk", Acta Obstetricia et Gynecologica Scandinavica, vol. 89, No. 5 •, May 2010, pp. 618-622.
Sarkar , "Mifepristone: Bioavailability, Pharmacokinetics and Use-Effectiveness", European Journal of Obstetrics & Gynecology and Reproductive Biology, vol. 101, No. 2, Mar. 10, 2002, pp. 113-120.
Sartor et al., "Mifepristone: Treatment of Cushing's Syndrome", Clinical Obstetrics and Gynecology, vol. 39, No. 2, Jun. 1996, pp. 506-510.
Schteingart , "Drugs in the Medical Treatment of Cushing's Syndrome", Expert Opinion on Emerging Drugs, vol. 14, No. 4, Dec. 2009, pp. 661-671.
Shi et al., "Pharmacokinetic Study of RU 486 and Its Metabolites After Oral Administration of Single Doses to Pregnant and Non-Pregnant Women", Clinical Article, Contraception, vol. 48, No. 2, Aug. 1993, pp. 133-149.
Sitruk-Ware et al., "Pharmacological Properties of Mifepristone: Toxicology and Safety in Animal and Human Studies", Contraception, vol. 68, No. 6, Dec. 2003, pp. 409-420.
Tran et al., "Translation of Drug Interaction Knowledge to Actionable Labeling", Clinical Pharmacology & Therapeutics, vol. 105, No. 6, Jun. 2019, pp. 1292-1295.
Tritos et al., "Medical Management of Cushing's Disease", Journal of Neuro-Oncology, vol. 117, 2014, pp. 407-414.
Truong et al., "Budget Impact of Pasireotide for the Treatment of Cushing's Disease, a Rare Endocrine Disorder Associated with Considerable Comorbidities", Journal of Medical Economics, vol. 17, No. 4, Apr. 2014, pp. 288-295.
Tsigos et al., "Differential Diagnosis and Management of Cushing's Syndrome", Annual Review of Medicine, vol. 47, 1996, pp. 443-461.
Tsunoda et al., "Differentiation of Intestinal and Hepatic Cytochrome P450 3A Activity with Use of Midazolam as an in Vivo Probe: Effect of Ketoconazole", Clinical Pharmacology and Therapeutics, vol. 66, No. 5, Nov. 1999, pp. 461-471.
Van Der Lelij , "Aspects of Medical Therapy of Neuroendocrine Disorders", Thesis, 1992, 166 pages.
Van Der Lely et al., "Rapid Reversal of Acute Psychosis in the Cushing Syndrome with the Cortisol-Receptor Antagonist Mifepristone (RU 486)", Annals of Internal Medicine, vol. 114, No. 2, Jan. 15, 1991, pp. 143-144.
Varis et al., "The Effect of Itraconazole on the Pharmacokinetics and Pharmacodynamics of Oral Prednisolone", European Journal of Clinical Pharmacology, vol. 56, No. 1, Apr. 2000, pp. 57-60.
Viera et al., "Potassium Disorders: Hypokalemia and Hyperkalemia", American Family Physician, vol. 92, No. 6, Sep. 15, 2015, pp. 487-495.

(56) References Cited

OTHER PUBLICATIONS

Von Moltke et al., "In Vitro Approaches to Predicting Drug Interactions In Vivo", Biochemical Pharmacology, vol. 55, No. 2, Jan. 15, 1998, pp. 113-122.
Von Moltke et al., "Metabolism of Drugs by Cytochrome P450 3A Isoforms", Clinical Pharmacokinetic,, vol. 29, 1995, pp. 33-44.
Wilkinson , "Pharmacokinetics: The Dynamics of Drug Absorption, Distribution and Elimination", Goodman & Gilmans' The Pharmacological Basis of Therapeutics, Tenth Edition, 2001, 30 pages.
Zhang et al., "Predicting Drug-Drug Interactions: An FDA Perspective", The AAPS Journal, vol. 11, No. 2, Jun. 2009, pp. 300-306.
"Amorphous Materials: How Some Solids Flow Like Liquids", Science Daily, CNRS, Available Online at: http://www.sciencedaily.com/releases/2008/07/080704153507.htm, Accessed from Internet on Jan. 16, 2014, pp. 1-3.
"Amorphous Solid", Wikepedia, Available Online at: http://en.wikipedia.org/wiki/Amorphous_solid, Jan. 16, 2014, pp. 1-3.
"Assessing the Effects of Food on Drugs in INDs and NDAs—Clinical Pharmacology Considerations Guidance for Industry", U.S. Department of Health and Human Services Food and Drug Administration Center for Drug Evaluation and Research (CDER), Jun. 2022, 18 pages.
"Chemical Processing", Available Online at: https://www.chemicalprocessing.com/, Dec. 13, 2019, pp. 1-8.
"Data Sheet: Glucocorticoid Receptor mouse monoclonal antibody NCL-GCR", Novocastra Laboratories Ltd., Available Online at: http://www.ebiotrade.com/buyf/Novocastra/data/hrerp/gcr.pdf, Accessed from internet at Jun. 7, 2011.
"Database Crossfile Beilstein", Beilstein Institut Zur Foerderung der Chemischen Wissenschaft, Accession No. 101172-52-5 (BRN), Jun. 27, 1988, 3 pages.
"Highlights of Prescribing Information", KORLYM® (Mifepristone), Concept Therapeutics Incorporated, 2017, pp. 1-7.
"Mifeprex (Mifepristone) Tablets, 200mg For Oral Administration Only", Mifeprex (Mifepristone) Label, Rev 2, Jul. 19, 2005, pp. 1-20.
"Preservatives and Antioxidants Database", Available Online at: Compounding Today.com | Preservatives and Antioxidants Database, Oct. 29, 2005, 3 pages.
"Propylene Glycol Monocaprylate Type II", Capryol® 90, Available Online at: https://www.gattefosse.com/pharmaceuticals-products/capryol-90, May 28, 2017, 3 pages.
"Safety, Tolerability, and Pharmacokinetic Study of CORT113176 in Healthy Participants", NCT04994743, Available Online at: https://classic.clinicaltrials.gov/ct2/history/NCT04994743?A=2&B=2&C=merged#StudyPageTop, Oct. 7, 2021, 7 pages.
"Study of Drug 1 (Enzalutamide) Plus Drug 2 (Relacorilant) for Patients With Prostate Cancer", ClinicalTrials.gov, Available Online at: www.clinicaltrials.gov/ct2/show/NCT03674814, Accessed from internet on Apr. 10, 2019, 9 pages.
"Study of Relacorilant in Combination with Nab-Paclitaxel for Patients with Recurrent Platinum-Resistant Ovarian, Fallopian Tube, or Primary Peritoneal Cancer", ClinicalTrials.gov, Available Online at: www.clinicaltrials.gov/ct2/show/NCT03776812, Jun. 7, 2021, 11 pages.
"Study to Evaluate Cort125134 in Combination with Nab-Paclitaxel in Patients with Solid Tumors", ClinicalTrials.gov, Available Online at: www.clinicaltrials.gov/ct2/show/NCT02762981, Accessed from internet on Apr. 30, 2019, 7 pages.
U.S. Appl. No. 12/777,340 , "Declaration Under 37 CFR 1.132 by Robin Clark", Solid Forms and Process for Preparing, Feb. 2013, 5 pages.
U.S. Appl. No. 13/001,211 , Final Office Action, Mailed On Jun. 7, 2013, 12 pages.
U.S. Appl. No. 13/001,211 , Non Final Office Action, Mailed On Dec. 21, 2012, 14 pages.
U.S. Appl. No. 13/901,946 , Non Final Office Action, Mailed On Apr. 1, 2014, 8 pages.
U.S. Appl. No. 13/901,946 , Notice of Allowance, Mailed On Jun. 26, 2014, 5 pages.
U.S. Appl. No. 14/020,205 , Advisory Action, Mailed On Dec. 19, 2016, 3 pages.
U.S. Appl. No. 14/020,205 , Final Office Action, Mailed On Jan. 23, 2015, 11 pages.
U.S. Appl. No. 14/020,205 , Final Office Action, Mailed On Oct. 20, 2016, 11 pages.
U.S. Appl. No. 14/020,205 , Final Office Action, Mailed On Nov. 1, 2017, 18 pages.
U.S. Appl. No. 14/020,205 , Final Office Action, Mailed On Nov. 26, 2018, 20 pages.
U.S. Appl. No. 14/020,205 , Final Office Action, Mailed On Sep. 10, 2019, 24 pages.
U.S. Appl. No. 14/020,205 , Non Final Office Action, Mailed On May 30, 2018, 19 pages.
U.S. Appl. No. 14/020,205 , Non Final Office Action, Mailed On May 30, 2014, 9 pages.
U.S. Appl. No. 14/020,205 , Non-Final Office Action, Mailed On Feb. 24, 2016, 12 pages.
U.S. Appl. No. 14/020,205 , Non-Final Office Action, Mailed On Apr. 21, 2017, 15 pages.
U.S. Appl. No. 14/020,205, Non-Final Office Action, Mailed On Apr. 2, 2019, 23 pages.
U.S. Appl. No. 14/172,051 , Non-Final Office Action, Mailed On Mar. 10, 2015, 9 pages.
U.S. Appl. No. 14/172,051 , Notice of Allowance, Mailed On Jun. 24, 2015, 11 pages.
U.S. Appl. No. 14/172,051 , Notice of Allowance, Mailed On Apr. 30, 2015, 5 pages.
U.S. Appl. No. 14/296,127 , Final Office Action, Mailed On Jul. 5, 2016, 9 pages.
U.S. Appl. No. 14/296,127 , Non-Final Office Action, Mailed On Dec. 17, 2015, 10 pages.
U.S. Appl. No. 14/296,127 , Non-Final Office Action, Mailed On Sep. 14, 2016, 7 pages.
U.S. Appl. No. 14/296,127 , Notice of Allowance, Mailed On Dec. 8, 2016, 9 pages.
U.S. Appl. No. 14/296,127 , "Restriction Requirement", Oct. 8, 2015, 11 pages.
U.S. Appl. No. 14/380,606 , Non-Final Office Action, Mailed On Aug. 24, 2015, 13 pages.
U.S. Appl. No. 14/380,606 , "Notice of Allowability", Dec. 11, 2015, 5 pages.
U.S. Appl. No. 14/380,606 , Notice of Allowance, Mailed On Nov. 20, 2015, 7 pages.
U.S. Appl. No. 14/380,606 , "Restriction Requirement", Jun. 30, 2015, 7 pages.
U.S. Appl. No. 14/451,207 , Advisory Action, Mailed On Jan. 23, 2015, 3 pages.
U.S. Appl. No. 14/451,207 , Advisory Action, Mailed On Nov. 17, 2015, 3 pages.
U.S. Appl. No. 14/451,207 , "Final Office action", Dec. 2, 2014, 11 pages.
U.S. Appl. No. 14/451,207 , Final Office Action, Mailed On Sep. 4, 2015, 9 pages.
U.S. Appl. No. 14/451,207 , Non-Final Office Action, Mailed On May 5, 2015, 10 pages.
U.S. Appl. No. 14/451,207 , Non-Final Office Action, Mailed On Feb. 24, 2016, 11 pages.
U.S. Appl. No. 14/451,207 , Non-Final Office Action, Mailed On Sep. 8, 2014, 17 pages.
U.S. Appl. No. 14/451,207 , Notice of Allowance, Mailed On Jan. 29, 2016, 5 pages.
U.S. Appl. No. 14/487,347 , Non-Final Office Action, Mailed On Apr. 14, 2015, 5 pages.
U.S. Appl. No. 14/487,347 , Notice of Allowance, Mailed On Oct. 14, 2015, 7 pages.
U.S. Appl. No. 14/549,885 , Final Office Action, Mailed On Mar. 25, 2016, 6 pages.
U.S. Appl. No. 14/549,885 , Final Office Action, Mailed On Mar. 7, 2017, 6 pages.
U.S. Appl. No. 14/549,885 , "First Hunt Declaration", Jan. 18, 2017, pp. 1-4.

(56) References Cited

OTHER PUBLICATIONS

U.S. Appl. No. 14/549,885 , Non Final Office Action, Mailed On Apr. 19, 2018, 12 pages.
U.S. Appl. No. 14/549,885 , Non-Final Office Action, Mailed On Apr. 6, 2015, 13 pages.
U.S. Appl. No. 14/549,885 , Non-Final Office Action, Mailed On Jul. 26, 2017, 14 pages.
U.S. Appl. No. 14/549,885 , Non-Final Office Action, Mailed On Aug. 7, 2015, 9 pages.
U.S. Appl. No. 14/549,885 , Notice of Allowance, Mailed On Jun. 19, 2018, 7 pages.
U.S. Appl. No. 14/549,885 , "Second Hunt Declaration", Jul. 7, 2017, 14 pages.
U.S. Appl. No. 15/013,218 , Non-Final Office Action, Mailed On Dec. 2, 2016, 8 pages.
U.S. Appl. No. 15/013,218 , Notice of Allowance, Mailed On Mar. 17, 2017, 5 pages.
U.S. Appl. No. 15/013,660 , Non-Final Office Action, Mailed On Mar. 31, 2016, 16 pages.
U.S. Appl. No. 15/013,660 , Non-Final Office Action, Mailed On Sep. 26, 2016, 9 pages.
U.S. Appl. No. 15/013,660 , Notice of Allowance, Mailed On Jun. 22, 2017, 8 pages.
U.S. Appl. No. 15/013,660 , Notice of Allowance, Mailed On Mar. 29, 2017, 8 pages.
U.S. Appl. No. 15/448,827 , Final Office Action, Mailed On Jul. 29, 2019, 6 pages.
U.S. Appl. No. 15/448,827 , Non-Final Office Action, Mailed On Mar. 1, 2019, 19 pages.
U.S. Appl. No. 15/448,827 , Notice of Allowance, Mailed On Aug. 15, 2019, 8 pages.
U.S. Appl. No. 15/448,827 , "Restriction Requirement", Dec. 13, 2018, 8 pages.
U.S. Appl. No. 15/621,013 , Non-Final Office Action, Mailed On Jan. 16, 2018, 7 pages.
U.S. Appl. No. 15/621,013 , Notice of Allowance, Mailed On Feb. 27, 2018, 5 pages.
U.S. Appl. No. 15/697,878 , Non-Final Office Action, Mailed On Jan. 12, 2018, 11 pages.
U.S. Appl. No. 15/697,878 , Notice of Allowance, Mailed On Feb. 23, 2018, 9 pages.
U.S. Appl. No. 15/704,726 , Non-Final Office Action, Mailed On Oct. 30, 2018, 10 pages.
U.S. Appl. No. 15/704,726 , Notice of Allowance, Mailed On Feb. 21, 2019, 8 pages.
U.S. Appl. No. 15/704,726 , "Restriction Requirement", Sep. 24, 2018, 6 pages.
U.S. Appl. No. 15/889,494 , Final Office Action, Mailed On Jun. 10, 2019, 7 pages.
U.S. Appl. No. 15/889,494 , Non-Final Office Action, Mailed On Jan. 2, 2019, 17 pages.
U.S. Appl. No. 15/889,494 , Notice of Allowance, Mailed On Jun. 28, 2019, 6 pages.
U.S. Appl. No. 15/915,477 , Final Office Action, Mailed On Aug. 13, 2018, 9 pages.
U.S. Appl. No. 15/915,477 , Non-Final Office Action, Mailed On Jun. 12, 2018, 11 pages.
U.S. Appl. No. 15/915,477 , Notice of Allowance, Mailed On Aug. 27, 2018, 11 pages.
U.S. Appl. No. 15/942,312 , Non Final Office Action, Mailed On Jul. 16, 2018, 15 pages.
U.S. Appl. No. 15/942,312 , Non-Final Office Action, Mailed On Feb. 20, 2019, 9 pages.
U.S. Appl. No. 15/942,312 , Notice of Allowance, Mailed On Jul. 29, 2019, 8 pages.
U.S. Appl. No. 15/942,312 , Notice of Allowance, Mailed On Nov. 7, 2018, 8 pages.
U.S. Appl. No. 16/036,001 , Non-Final Office Action, Mailed On Oct. 8, 2019, 11 pages.
U.S. Appl. No. 16/036,001 , Non-Final Office Action, Mailed On Apr. 26, 2019, 18 pages.
U.S. Appl. No. 16/036,001 , "Restriction Requirement", Apr. 8, 2019, 7 pages.
U.S. Appl. No. 16/150,916 , Non-Final Office Action, Mailed On Nov. 1, 2018, 10 pages.
U.S. Appl. No. 16/150,916 , Notice of Allowance, Mailed On Jan. 11, 2019, 8 pages.
U.S. Appl. No. 16/161,642 , Non-Final Office Action, Mailed On Feb. 13, 2019, 11 pages.
U.S. Appl. No. 16/161,642 , "Notice of Allowability", May 17, 2019, 2 pages.
U.S. Appl. No. 16/161,642 , Notice of Allowance, Mailed On Apr. 8, 2019, 5 pages.
U.S. Appl. No. 16/161,642 , "Restriction Requirement", Dec. 19, 2018, 5 pages.
U.S. Appl. No. 16/185,271 , Non-Final Office Action, Mailed On Jun. 3, 2019, 17 pages.
U.S. Appl. No. 16/185,271 , Notice of Allowance, Mailed On Oct. 25, 2019, 8 pages.
U.S. Appl. No. 16/260,360 , Non-Final Office Action, Mailed On Mar. 28, 2019, 9 pages.
U.S. Appl. No. 16/260,360 , Notice of Allowance, Mailed On Jul. 3, 2019, 8 pages.
U.S. Appl. No. 16/570,839 , Final Office Action, Mailed On Sep. 30, 2020, 8 pages.
U.S. Appl. No. 16/570,839 , Non-Final Office Action, Mailed On Jun. 15, 2020, 12 pages.
U.S. Appl. No. 16/570,839 , Notice of Allowance, Mailed On Dec. 14, 2020, 7 pages.
U.S. Appl. No. 16/719,644 , Non-Final Office Action, Mailed On Nov. 18, 2021, 16 pages.
U.S. Appl. No. 16/719,644 , Notice of Allowance, Mailed On Jun. 3, 2022, 10 pages.
U.S. Appl. No. 16/719,644 , Notice of Allowance, Mailed On Jul. 28, 2022, 8 pages.
U.S. Appl. No. 16/742,198 , Non-Final Office Action, Mailed On May 1, 2020, 3 pages.
U.S. Appl. No. 16/742,198 , Notice of Allowance, Mailed On Aug. 21, 2020, 8 pages.
U.S. Appl. No. 16/742,198 , "Supplemental Notice of Allowability", Sep. 10, 2020, 2 pages.
U.S. Appl. No. 17/072,493 , Non-Final Office Action, Mailed On Dec. 6, 2022, 12 pages.
U.S. Appl. No. 17/110,170 , Non-Final Office Action, Mailed On Nov. 28, 2022, 9 pages.
U.S. Appl. No. 17/110,170 , Notice of Allowance, Mailed On Mar. 29, 2023, 8 pages.
U.S. Appl. No. 17/110,170 , "Supplemental Notice of Allowability", Apr. 10, 2023, 2 pages.
U.S. Appl. No. 17/950,902 , Non-Final Office Action, Mailed On Jun. 15, 2023, 19 pages.
U.S. Appl. No. 17/950,902 , "Supplemental Notice of Allowability", Jan. 26, 2024, 2 pages.
U.S. Appl. No. 18/121,694 , Non-Final Office Action, Mailed On Sep. 6, 2024, 13 pages.
U.S. Appl. No. 18/136,210 , Non-Final Office Action, Mailed On Oct. 24, 2024, 10 pages.
U.S. Appl. No. 18/136,210 , Notice of Allowance, Mailed On Feb. 13, 2025, 8 pages.
U.S. Appl. No. 18/427,477 , Non-Final Office Action, Mailed On May 21, 2025, 11 pages.
U.S. Appl. No. 18/427,477 , Notice of Allowance, Mailed On Nov. 19, 2025, 8 pages.
U.S. Appl. No. 18/496,134 , Advisory Action, Mailed On Jun. 3, 2024, 3 pages.
U.S. Appl. No. 18/496,134 , Final Office Action, Mailed On Mar. 26, 2024, 14 pages.
U.S. Appl. No. 18/496,134 , Final Office Action, Mailed On Jan. 27, 2025, 16 pages.
U.S. Appl. No. 18/496,134 , Non-Final Office Action, Mailed On Dec. 15, 2023, 12 pages.

(56) References Cited

OTHER PUBLICATIONS

U.S. Appl. No. 18/496,134 , Non-Final Office Action, Mailed On Aug. 13, 2024, 13 pages.
U.S. Appl. No. 18/496,134 , Notice of Allowance, Mailed On Jul. 11, 2025, 8 pages.
Aherne et al., "Finding the Needle in the Haystack: Why Highthroughput Screening is Good for Your Health", Breast Cancer Research, vol. 4, No. 4, Aug. 2002, pp. 148-154.
Aisen et al., "A Randomized Controlled Trial of Prednisone in Alzheimer's Disease. Alzheimer's Disease Cooperative Study", Neurology, vol. 54, No. 3, Feb. 8, 2000, pp. 1-2.
Akiyama et al., "Inflammation and Alzheimer's Disease", Neurobiology of Aging, vol. 21, No. 3, May-Jun. 2000, 66 pages.
Amiri-Kordestani et al., "Targeting MDR in Breast and Lung Cancer: Discriminating Its Potential Importance From the Failure of Drug Resistance Reversal Studies", Drug Resistance Updates, vol. 15, No. 0, Feb. 2012, pp. 50-61.
Antonarakis et al., "Emerging Therapeutic Approaches in the Management of Metastatic Castration Resistant Prostate Cancer", Prostate Cancer and Prostatic Diseases, vol. 14, No. 3, Sep. 2011, pp. 206-218.
Arora et al., "Glucocorticoid Receptor Confers Resistance to Antiandrogens by Bypassing Androgen Receptor Blockade", Cell, vol. 155, No. 6, Dec. 5, 2013, pp. 1309-1322.
Arrat et al., "ACTH (Acthar Gel) Reduces Toxic SOD1 Protein Linked to Amyotrophic Lateral Sclerosis in Transgenic Mice: A Novel Observation", Public Library of Science One, vol. 10, No. 5, May 8, 2015, pp. 1-12.
Israeli Patent Application No. 245848 , Office Action, Mailed On Jul. 18, 2018, 6 pages.
Attard et al., "Translating Scientific Advancement into Clinical Benefit for Castration-Resistant Prostate Cancer Patients", Clinical Cancer Research, vol. 1, No. 12, Jun. 15, 2011, pp. 3867-3875.
Australian Patent Application No. 2013266110 , First Examiner Report, Mailed On Sep. 19, 2016, 2 pages.
Australian Patent Application No. 2013266110 , "Notice of Acceptance", Apr. 7, 2017, 3 pages.
Australian Patent Application No. 2014352915 , "First Examination Report", Feb. 6, 2018, 2 pages.
Australian Patent Application No. 2017323636 , "First Examination Report", Jul. 22, 2019, 4 pages.
Australian Patent Application No. 2017323636 , "Second Examination Report", Nov. 18, 2019, 3 pages.
Australian Patent Application No. 2018244928 , "First Examination Report", Feb. 14, 2023, 5 pages.
Australian Patent Application No. 2018244928 , "Notice of Acceptance", Oct. 5, 2023, 3 pages.
Australian Patent Application No. 2018244928 , "Second Examination Report", Jun. 16, 2023, 4 pages.
Barth et al., "Structural and Stereoelectronic Requirements for the Inhibition of Mammalian 2,3-Oxidosqualene Cyclase by Substituted Isoquinoline Derivatives", Journal of Medicinal Chemistry, vol. 39, No. 12, Jun. 7, 1996, pp. 2302-2312.
Behl et al., "Protection Against Oxidative Stress-Induced Neuronal Cell Death—A Novel Role for RU486", European Journal of Neuroscience, vol. 9, No. 5, May 1997, pp. 912-920.
Belanoff et al., "Selective Glucocorticoid Receptor (Type II) Antagonists Prevent Weight Gain Caused by Olanzapine in Rats", European Journal of Pharmacology, vol. 655, No. 1-3, Mar. 25, 2011, pp. 117-120.
Belova et al., "Glucocorticoid Receptor Expression in Breast Cancer Associates with Older Patient Age", Breast Cancer Research and Treatment, vol. 116, No. 3, Aug. 2009, pp. 441-447.
Benagiano et al., "Selective Progesterone Receptor Modulators 3: Use in Oncology, Endocrinology and Psychiatry", Expert Opinion on Pharmacotherapy, vol. 9, No. 14, Oct. 2008, pp. 2487-2496.
Block et al., "Glucocorticoid Receptor Expression In 20 Solid Tumor Types Using Immunohistochemistry Assay", Cancer Management and Research, vol. 9, Mar. 6, 2017, pp. 65-72.
Bolton et al., "Cell- and Gene-Specific Regulation of Primary Target Genes by the Androgen Receptor". Genes & Development, vol. 21, No. 16, Aug. 15, 2007, pp. 2005-2017.
Bolton et al., "The Effects of the Anti-Glucocorticoid RU 38486 on Steroid- Abstract Mediated Suppression of Experimental Allergic Encephalomyelitis (EAE) in the Lewis Rat", Life Sciences, vol. 45, No. 1, 1989, pp. 97-104.
Brazilian Patent Application No. 112014028857-7 , Office Action, Mailed On Dec. 2, 2019, 4 pages.
Brazilian Patent Application No. 112016011826-0 , Office Action, Mailed On Apr. 8, 2020, 4 pages.
Brusaferri et al., "Steroids for Multiple Sclerosis and Optic Neuritis: A Meta- Abstract Analysis of Randomized Controlled Clinical Trials", Journal of Neurology, vol. 247, No. 6, Jun. 2000, pp. 435-442.
Canadian Patent Application No. 2,728,563 , Notice of Allowance, Mailed On Oct. 18, 2016, 1 page.
Canadian Patent Application No. 2,728,563 , Office Action, Mailed On Feb. 1, 2016, 3 pages.
Canadian Patent Application No. 2,872,260, Notice of Allowance, Mailed On Sep. 30, 2020, 1 page.
Canadian Patent Application No. 2,872,260 , Office Action, Mailed On Apr. 14, 2020, 3 pages.
Canadian Patent Application No. 2,872,260 , Office Action, Mailed On Jun. 7, 2019, 3 pages.
Canadian Patent Application No. 2,872,260 , Office Action, Mailed On Nov. 30, 2018, 3 pages.
Canadian Patent Application No. 2,872,260, Office Action, Mailed On Oct. 7, 2019, 3 pages.
Canadian Patent Application No. 2728563 , Office Action, Mailed On Jun. 5, 2015, 3 pages.
Canadian Patent Application No. 3,034,114 , Office Action, Mailed On Apr. 9, 2020, 5 pages.
Canadian Patent Application No. 3,055,076 , Notice of Allowance, Mailed On Nov. 19, 2021, 1 page.
Canadian Patent Application No. 3,055,076 , Office Action, Mailed On Mar. 25, 2021, 3 pages.
Canadian Patent Application No. 3,121,193, Office Action, Mailed On Sep. 14, 2022, 4 pages.
Caccamo et al., "Glucocorticoids Exacerbate Cognitive Deficits in TDP-25 Transgenic Mice Via a Glutathionemediated Mechanism: Implications for Aging, Stress and TDP-43 Proteinopathies", The Journal of Neuroscience, vol. 33, No. 3, Jan. 16, 2013, pp. 906-913.
Carri et al., "Neurodegeneration in Amyotrophic Lateral Sclerosis: The Role of Oxidative Stress and Altered Homeostasis of Metals", Brain Research Bulletin, vol. 61, No. 4, Aug. 30, 2003, pp. 365-374.
Chan et al., "Prognostic Significance of Gleason Score 3+4 versus Gleason Score 4+3 Tumor at Radical Prostatectomy", Adult Urology, vol. 56, No. 5, Nov. 2000, pp. 823-827.
Check et al., "Evidence that Mifepristone, A Progesterone Receptor Antagonist, Can Cross the Blood Brain Barrier and Provide Palliative Benefits for Glioblastoma Multiforme Grade IV", Anticancer Research, vol. 34, No. 5, May 2014, pp. 2385-2388.
Check et al., "Mifepristone Causing Complete Remission of Rapidly Advancing Leukemia with Measurement of Progesterone-Induced Blocking Factor", Anticancer Research, vol. 34, No. 5, May 2014, pp. 2413-2416.
Chen et al., "Androgen and Glucocorticoid Receptor Heterodimer Formation: A Possible Mechanism for Mutual Inhibition of Transcriptional Activity", Journal of Biological Chemistry, vol. 272, No. 22, May 30, 1997, pp. 14087-14092.
Chen et al., "Mechanism of the Reversal Effect of Mifepristone on Drug Resistance of the Human Cervical Cancer Cell Line HELA/MMC", Genetics and Molecular Research, vol. 13, No. 1, Feb. 27, 2014, pp. 1288-1295.
Chi et al., "Castration-Resistant Prostate Cancer: From New Pathophysiology to New Treatment Targets", European Urology, vol. 56, No. 4, Oct. 2009, pp. 594-605.
Cho et al., "Role of Activation function Domain-1, DNA Binding, and Coactivator GRIP1 in the Expression of Partial Agonist Activity of Glucocorticoid Receptor-Antagonist Complexes", Biochemistry, vol. 44, No. 9, Mar. 8, 2005, pp. 3547-3561.

(56) References Cited

OTHER PUBLICATIONS

Christoffers et al., "Absolute Configuration of Methyl (+)-1,2,3,4,6,7,8,8a-Octahydro-6-Isoquinolone-8a-Carboxylate and Stereochemistry of a Copper-Catalyzed Asymmetric Michael Reaction", Zeitschrift Fuer Naturforschung B Chemical Sciences, vol. 59, No. 4, Apr. 1, 2004, pp. 375-379.
Christoffers et al., "Copper-Catalyzed Asymmetric Michael Reactions with a-Amino Acid Amides: Synthesis of an Optically Active Piperidine Derivative", Wiley Online Library, vol. 2002, No. 9, May 2002, pp. 1505-1508.
Christoffers et al., "Synthesis of an Optically Active Decahydro-6-Isoquinolone Scaffold with a Quaternary Stereocenter", Wiley Online Library, vol. 2004, No. 12, Jun. 2004, pp. 2701-2706.
Christoffers , "Transformation of an Optically Active Decahydro-6-isoquinolone Scaffold: Perfect Felkin-Anh Diastereoselectivity", Organic Letters, vol. 6, No. 7, Feb. 3, 2004, pp. 1171-1173.
Chu , "Connecting Via Winsock to SIN at PTO-STN on Port 23", STN-12691012, STN International, Mar. 19, 2012, 62 pages.
Chu et al., "Successful Long-Term Treatment of Refractory Cushing's Disease with High-Dose Mifepristone (RU 486)", The Journal of Clinical Endocrinology & Metabolism, vol. 86, No. 8, Aug. 2001, pp. 3568-3573.
Chilean Patent Application No. 2014-03173 , Substantive Examination Report, Mailed On Feb. 11, 2016, 11 pages.
Chilean Patent Application No. 2014-03173 , Substantive Examination Report, Mailed On Sep. 19, 2016, 6 pages.
Chilean Patent Application No. 201900569 , Substantive Examination Report, Mailed On Mar. 6, 2019, 8 pages.
Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, No. 4, Feb. 15, 2008, pp. 1312-1317.
Clark et al., "2-Benzenesulfonyl-8a-Benzyl-Hexahydro-2h-Isoquinolin-6-ones as Selective Glucocorticoid Receptor Antagonists", Bioorganic & Medicinal Chemistry Letters, vol. 17, No. 20, Oct. 15, 2007, pp. 5704-5708.
CLARK , "Glucocorticoid Receptor Antagonists", Current Topics in Medicinal Chemistry, vol. 8, No. 9, Jun. 1, 2008, pp. 813-838.
Cleutjens et al., "Both Androgen Receptor and Glucocorticoid Receptor are Able to Induce Prostate-Specific Antigen Expression, but Differ in their Growth-Stimulating Properties of LNCaP Cells", Endocrinology, vol. 138, No. 12, Dec. 1, 1997, pp. 5293-5300.
Chinese Patent Application No. 201380039218.1 , "Notice of Decision To Grant", Aug. 29, 2018, 4 pages.
Chinese Patent Application No. 201380039218.1 , Office Action, Mailed On Nov. 30, 2016, 10 pages.
Chinese Patent Application No. 201380039218.1 , Office Action, Mailed On Jan. 6, 2016, 14 pages.
Chinese Patent Application No. 201380039218.1 , Office Action, Mailed On Dec. 12, 2017, 7 pages.
Chinese Patent Application No. 201380039218.1 , Office Action, Mailed On Jun. 16, 2017, 9 pages.
Chinese Patent Application No. 201480074087.5 , Notice of Decision to Grant, Mailed On Jan. 31, 2019, 5 pages.
Chinese Patent Application No. 2014800740875 , Office Action, Mailed On Mar. 26, 2018, 16 pages.
Chinese Patent Application No. 201880023127.1 , Notice of Decision to Grant, Mailed On May 29, 2023, 6 pages.
Chinese Patent Application No. 201880023127.1 , Office Action, Mailed On May 6, 2022, 21 pages.
Chinese Patent Application No. 201880023127.1 , Office Action, Mailed On Jan. 18, 2023, 23 pages.
Chinese Patent Application No. 201980084873.6 , Office Action, Mailed On Jul. 8, 2022, 7 pages.
Colombian Patent Application No. 14-256677 , Office Action, Mailed On Jan. 4, 2016, 7 pages.
Colombian Patent Application No. 14-256677 , Substantive Examination Report, Mailed On Oct. 7, 2015, 7 pages.
Colleoni et al., "Response to Primary Chemotherapy in Breast Cancer Patients with Tumors not Expressing Estrogen and Progesterone Receptors", Annals of Oncology, vol. 11, No. 8, Aug. 1, 2000, pp. 1057-1059.
Cossu et al., "The Role of Mifepristone in Meningiomas Management: A Systematic Review of the Literature", BioMed Research International, vol. 2015, Jul. 2015, pp. 1-11.
Cummings et al., "Treatment Combinations for Alzheimer's Disease: Current and Future Pharmacotherapy Options", Journal of Alzheimer's Disease, vol. 67, Jan. 2019, pp. 779-794.
Damia et al., "Contemporary Pre-Clinical Development of Anticancer Agents—What are the Optimal Preclinical Models", European Journal of Cancer, vol. 45, No. 16, Nov. 2009, pp. 2768-2781.
Davies et al., "Association of Glucocorticoid Receptors with Prostate Nuclear Sites for Androgen Receptors and with Androgen Response Elements", Journal of Molecular Endocrinology, vol. 5, No. 2, Oct. 1, 1990, pp. 117-127.
De Bono et al., "Abiraterone and Increased Survival in Metastatic Prostate Cancer", New England Journal of Medicine, vol. 364, No. 21, May 26, 2011, pp. 1995-2005.
Dennis , "Off by a Whisker", Nature, vol. 442, Aug. 7, 2006, pp. 739-741.
Desmedt et al., "Strong Time Dependence of the 76-Gene Prognostic Signature for Node-Negative Breast Cancer Patients in the TRANSBIG Multicenter Independent Validation Series", Clinical Cancer Research, vol. 13, No. 11, Jun. 1, 2007, pp. 3207-3214.
Di Lorenzo et al., "Castration-Resistant Prostate Cancer", Drugs, vol. 70, No. 8, May 2010, pp. 983-1000.
Dibas et al., "Glucocorticoid Therapy and Ocular Hypertension", European Journal of Pharmacology, vol. 787, Sep. 15, 2016, pp. 1-33.
Dinkel et al., "Novel Glucocorticoid Effects on Acute Inflammation in the CNS", Journal of Neurochemistry, vol. 84, Feb. 2003, pp. 705-716.
Donovan et al., "Androgen Receptor Expression is Associated with Prostate Cancer-Specific Survival in Castrate Patients with Metastatic Disease", Bob Jones University International, vol. 105, No. 4, Feb. 2010, pp. 462-467.
Efstathiou et al., "Molecular Characterization of Enzalutamide-treated Bone Metastatic Castration-resistant Prostate Cancer", European Urology, vol. 67, No. 1, Jan. 2015, pp. 53-60.
Elmore et al., "Nonsteroidal Selective Glucocorticoid Modulators: The Effect of C-5 Alkyl Substitution on the Transcriptional Activation/Repression Profile of 2,5-Dihydro-10-Methoxy-2,2,4-Trimethyl-1H-[1]Benzopyrano[3,4-f]Quinolines", American Chemical Society, Journal of Medicinal Chemistry, vol. 44, No. 25, Dec. 1, 2001, pp. 4481-4491.
European Patent Application No. 09774351.2 , Extended European Search Report, Mailed On May 7, 2012, 7 pages.
European Patent Application No. 13751132.5 , Extended European Search Report, Mailed On Mar. 21, 2016, 14 pages.
European Patent Application No. 13751132.5 , "Partial Supplementary European Search Report", Sep. 7, 2015, 6 pages.
European Patent Application No. 13793417.0 , "Decision to Grant", Jan. 5, 2018, 3 pages.
European Patent Application No. 13793417.0 , Extended European Search Report, Mailed On Jan. 4, 2016, 7 pages.
European Patent Application No. 13793417.0 , Office Action, Mailed On Oct. 11, 2016, 4 pages.
European Patent Application No. 14863514.7 , Extended European Search Report, Mailed On May 4, 2017, 6 pages.
European Patent Application No. 14863514.7 , Notice of Decision to Grant, Mailed On Jun. 27, 2019, 2 pages.
European Patent Application No. 16183642.4 , Extended European Search Report, Mailed On Dec. 1, 2016, 12 pages.
European Patent Application No. 16183642.4 , Ofice Action, Mailed On May 15, 2019, 7 pages.
European Patent Application No. 17760608.4 , Extended European Search Report, Mailed On Oct. 9, 2019, 10 pages.
European Patent Application No. 17849673.3 , Extended European Search Report, Mailed On Mar. 26, 2020, 11 pages.
European Patent Application No. 18154256.4 , Extended European Search Report, Mailed On Mar. 26, 2018, 6 pages.

(56) References Cited

OTHER PUBLICATIONS

European Patent Application No. 18154256.4 , Notice of Decision to Grant, Mailed On Aug. 16, 2019, 3 pages.
European Patent Application No. 18777520.0 , Extended European Search Report, Mailed On Jul. 16, 2020, 9 pages.
European Patent Application No. 18777520.0 , Office Action, Mailed On May 22, 2024, 4 pages.
European Patent Application No. 19177963.6 , Extended European Search Report, Mailed On Jul. 25, 2019, 5 pages.
European Patent Application No. 19188885.8 , Extended European Search Report, Mailed On Oct. 28, 2019, 6 pages.
European Patent Application No. 19188885.8 , Notice of Decision to Grant, Mailed On Feb. 18, 2021, 3 pages.
European Patent Application No. 19898009.6 , Extended European Search Report, Mailed On Sep. 8, 2022, 14 pages.
European Patent Application No. 21154665.0 , Extended European Search Report, Mailed On Apr. 23, 2021, 5 pages.
Evans et al., "CNS-Targeted Glucocorticoid Reduces Pathology in Mouse Model of Amyotrophic Lateral Sclerosis", Acta Neuropathologica Communications, vol. 2, No. 66, Jun. 13, 2014, pp. 1-13.
Fakih et al., "Glucocorticoids and Treatment of Prostate Cancer: A Preclinical and Clinical Review", Urology, vol. 60, No. 4, Oct. 2002, pp. 553-561.
Fidler et al., "Disease Progression in a Mouse Model of Amyotrophic Lateral Sclerosis: The Influence of Chronic Stress and Corticosterone", The Federation of American Societies for Experimental Biology (FASEB) Journal, vol. 25, Dec. 2011, pp. 4369-4377.
Fiorentino et al., "Blood and Tissue Biomarkers in Prostate Cancer: State of the Art", Urologic Clinics of North America, vol. 37, No. 1, Feb. 2010, pp. 1-14.
Flexner et al., "HIV Drug Development: The Next 25 Years", Nature Reviews, Drug Discovery, Dec. 2007, pp. 959-966.
Fradet, "PSA and Beyond: Biomarkers in Prostate Cancer Diagnosis and Prognosis", Current Opinion in Urology, vol. 19, No. 3, May 2009, pp. 243-246.
Gaddy et al., "Mifepristone Induces Growth Arrest, Caspase Activation, and Apoptosis of Estrogen Receptor-Expressing, Antiestrogen-Resistant Breast Cancer Cells", Clinical Cancer Research, vol. 10, No. 15, Aug. 1, 2004, pp. 5215-5225.
Gargiulo-Monachelli et al., "Circulating Gonadal and Adrenal Steroids in Amyotrophic Lateral Sclerosis: Possible Markers of Susceptibility and Outcome", Hormone and Metabolic Research, vol. 46, Jun. 2014, pp. 433-439.
Genck, "Make the Most of Antisolvent Crystallization: A Number of Factors Can Affect Solids' Formation", Chemical Processing, vol. 73, No. 12, Nov. 8, 2010, 8 pages.
Ghoumari et al., "Mifepristone (RU486) Protects Purkinje Cells from Cell Death in Organotypic Slice Cultures of Postnatal Rat and Mouse Cerebellum", Proceedings of the National Academy of Sciences, vol. 100, No. 13, Jun. 24, 2003, pp. 7953-7958.
Gonzalez et al., "Glucocorticoid Receptors and Actions in the Spinal Cord of the Wobbler Mouse, A Model for Neurodegenerative Diseases", Journal of Steroid Biochemistry and Molecular Biology, vol. 60, Nos. 3-4, Feb. 1997, pp. 205-213.
Grover et al., "The Initiation of Breast and Prostate Cancer", Carcinogenesis, vol. 23, No. 7, Jul. 1, 2002, pp. 1095-1102.
GULLIVER , "Xenobiotics and the Glucocorticoid Receptor", Toxicology and Applied Pharmacology, vol. 319, Mar. 15, 2017, pp. 69-79.
Guo et al., "A Novel Androgen Receptor Splice Variant Is Up-Regulated During Prostate Cancer Progression and Promotes Androgen Depletion-Resistant Growth", Cancer Research, vol. 69, No. 6, Mar. 15, 2009, pp. 2305-2313.
Gupta et al., "Studies on Carboxylation in Heterocyclic Systems", Journal of Scientific and Industrial Research, vol. 20B, Aug. 1961, pp. 394-397.
Gura , "Systems for Identifying New Drugs are Often Faulty", Science, Cancer Models, vol. 278, No. 5340, Nov. 7, 1997, pp. 1041-1042.
Han et al., "Biochemical (Prostate Specific Antigen) Recurrence Probability Following Radical Prostatectomy for Clinically Localized Prostate Cancer", The Journal of Urology, vol. 169, No. 2, Feb. 2003, pp. 517-523.
He et al., "Discovery of a Highly Potent Glucocorticoid for Asthma Treatment", Cell Discovery, vol. 1, No. 1, Dec. 15, 2015, pp. 1-13.
Hein et al., "Click Chemistry, A powerful Tool for Pharmaceutical Sciences", Pharmaceutical Research, vol. 25, No. 10, Oct. 2008, pp. 2216-2230.
Hemmi et al., "Dramatic Response of Dropped Head Sign to Treatment with Steroid in Parkinson's Disease: Report of Three Cases", Internal Medicine, vol. 50, Jan. 2011, pp. 757-761.
Henderson et al., "Estrogens as a Cause of Human Cancer: The Richard and Hinda Rosenthal Foundation Award Lecture", Cancer Research, vol. 48, No. 2, Jan. 15, 1988, pp. 246-253.
Hinrichs et al., "Glucocorticoids Do Not Inhibit Antitumor Activity of Activated CD8+ T Cells", Journal of Immunotherapy, vol. 28, No. 6, Nov. 1, 2005, pp. 1-17.
Ho et al., "A Complex Response Element in Intron 1 of the Androgen-Regulated 20-kDa Protein Gene Displays Cell Type-Dependent Androgen Receptor Specificity", Journal of Biological Chemistry, vol. 268, No. 36, Dec. 25, 1993, pp. 27226-27235.
Hsin et al., "Stereoselective Synthesis of Morphine Fragments Trans- and Cis-Octahydro-1H-Benzo[4,5]Furo[3,2-e]lsoquinolines", Tetrahedron, vol. 61, No. 2, Jan. 10, 2005, pp. 513-520.
Huang et al., "Reversal Effect of Mifepristone on Adriamycin Resistance in Human Breast Cancer Cell Line MCF-7/ADM in Vitro and in Vivo", Journal of Central South University, Medical Sciences, vol. 35, No. 6, Jun. 1, 2010, pp. 576-583.
Hunt et al., "1H-Pyrazolo[3,4-g]Hexahydro-Isoquinolines as Potent GR Antagonists with Reduced hERG Inhibition and an Improved Pharmacokinetic Profile", Bioorganic & Medicinal Chemistry Letters, vol. 25, No. 24, Dec. 15, 2015, pp. 5720-5725.
Hunt et al., "Assessment of Safety, Tolerability, Pharmacokinetics, and Pharmacological Effect of Orally Administered CORT125134: An Adaptive, Double-Blind, Randomized, Placebo-Controlled Phase 1 Clinical Study", Clinical Pharmacology in Drug Development, vol. 7, No. 4, May 2018, pp. 408-421.
Hunt , "Curriculum Vitae", 4 pages.
Hunt et al., "Identification of the Clinical Candidate (R)-(1-(4-Fluorophenyl)-6-((1-Methyl-1H-Pyrazol-4-yl)Sulfonyl)-4,4a,5,6,7,8-Hexahydro-1H-Pyrazolo[3,4-g]lsoquinolin-4a-yl)(4-(Trifluoromethyl)Pyridin-2-yl) (CORT125134): A Selective Glucocorticoid Receptor (GR) Anta", Journal of Medicinal Chemistry, vol. 60, No. 8, Apr. 27, 2017, pp. 3405-3421.
Hunt et al., "Preclinical Efficacy of the Selective GR Antagonist, CORT125134", American Association for Cancer Research, vol. 77, Jul. 1, 2017, 3 pages.
Israeli Patent Application No. 235868 , Notice of Allowance, Mailed On Oct. 23, 2017, 4 pages.
Israeli Patent Application No. 235868 , Office Action, Mailed On Aug. 4, 2015, 2 pages.
Israeli Patent Application No. 235868 , Office Action, Mailed On Jan. 23, 2017, 2 pages.
Israeli Patent Application No. 235868 , Office Action, Mailed On Jun. 14, 2017, 2 pages.
Israeli Patent Application No. 235868 , Office Action, Mailed On Jul. 25, 2016, 3 pages.
Israeli Patent Application No. 245848 , Notice of Allowance, Mailed On May 14, 2020, 5 pages.
Israeli Patent Application No. 245848, Office Action, Mailed On Jun. 10, 2019, 5 pages.
Israeli Patent Application No. 269725 , Notice of Allowance, Mailed On Apr. 21, 2020, 4 pages.
Indian Patent Application No. 10279/DELNP/2014 , "First Examination Report", Jul. 17, 2018, 5 pages.
Indian Patent Application No. 201617021323 , "First Examination Report", Feb. 20, 2020, 6 pages.
Indian Patent Application No. 201917007769 , "First Examination Report", Feb. 12, 2020, 6 pages.
Indian Patent Application No. 202117031274 , "First Examination Report", Dec. 29, 2021, 5 pages.

(56) References Cited

OTHER PUBLICATIONS

Isikbay et al., "Glucocorticoid Receptor Activity Contributes to Resistance to Androgen-Targeted Therapy in Prostate Cancer", Hormones and Cancer, vol. 5, No. 2, Mar. 2014, pp. 72-89.
Jannin et al., "Polyoxylglycerides and Glycerides: Effects of Manufacturing Parameters on API Stability, Excipient Functionality and Processing", International Journal of Pharmaceutics, vol. 466, May 15, 2014, pp. 109-121.
Jemal et al., "Cancer Statistics", CA: A Cancer Journal for Clinicians, vol. 60, No. 5, Sep. 2010, pp. 277-300.
Johnson et al., "Relationships Between Drug Activity in NCI Preclinical in Vitro and in Vivo Models and Early Clinical Trials", British Journal of Cancer, vol. 84, No. 10, May 18, 2001, pp. 1424-1431.
Japanese Patent Application No. 2007-503030 , Office Action, Mailed On Feb. 23, 2011, 8 pages.
Japanese Patent Application No. 2015-514233 , Notice of Allowance, Mailed On Jun. 29, 2017, 3 pages.
Japanese Patent Application No. 2015-514233, Office Action, Mailed On Jan. 23, 2017, 4 pages.
Japanese Patent Application No. 2016-533614 , Notice of Allowance, Mailed On Apr. 10, 2019, 5 pages.
Japanese Patent Application No. 2016-533614 , Office Action, Mailed On Jan. 17, 2019, 7 pages.
Japanese Patent Application No. 2016-533614 , Office Action, Mailed On Jul. 10, 2018, 8 pages.
Japanese Patent Application No. 2017-206081 , Office Action, Mailed On Apr. 4, 2018, 2 pages.
Japanese Patent Application No. 2017-206081 , Office Action, Mailed On Mar. 19, 2019, 2 pages.
Japanese Patent Application No. 2018-545599 , Office Action, Mailed On Oct. 16, 2019, 10 pages.
Japanese Patent Application No. 2019-552958 , Notice of Decision to Grant, Mailed On Sep. 20, 2024, 2 pages.
Japanese Patent Application No. 2019-552958 , Office Action, Mailed On Jul. 1, 2022, 11 pages.
Japanese Patent Application No. 2019-552958, Office Action, Mailed On Jan. 26, 2022, 9 pages.
Japanese Patent Application No. 2019-552958 , Office Action, Mailed On May 1, 2024, 9 pages.
Japanese Patent Application No. 2019-63279 , Office Action, Mailed On Mar. 31, 2020, 2 pages.
Japanese Patent Application No. 2021-536303 , Office Action, Mailed On Sep. 27, 2022, 6 pages.
Japanese Patent Application No. 2022-53345 , Office Action, Mailed On Mar. 16, 2023, 1 page.
Japanese Patent Application No. 2022-53345 , Office Action, Mailed On Sep. 25, 2024, 1 page.
Japanese Patent Application No. 2022-53345 , Office Action, Mailed On Dec. 8, 2023, 3 pages.
Kach et al., "Glucocorticoid Receptor Signaling in Breast and Prostate Cancers: Emergence as a Therapeutic Target", Science Translational Medicine, vol. 7, No. 305, Sep. 16, 2015, 9 pages.
Kach et al., "Selective Glucocorticoid Receptor Modulators (SGRMs) Delay Castrate- Resistant Prostate Cancer Growth", Molecular Cancer Therapeutics, vol. 16, No. 8, Aug. 2017, pp. 1680-1692.
Kadmiel et al., "Glucocorticoid Receptor Signaling in Health and Disease", Trends in Pharmacological Sciences, vol. 34, No. 9, Sep. 1, 2013, pp. 518-530.
Karantanos et al., "Understanding the Mechanisms of Androgen Deprivation Resistance in Prostate Cancer at the Molecular Level", European Urology, vol. 67, No. 1, Mar. 2015, pp. 470-479.
Keen et al., "The Biology of Breast Carcinoma", Cancer: Interdisciplinary International Journal of the American Cancer Society, vol. 97, No. 3, Feb. 1, 2003, pp. 825-833.
Kim et al., "Current Treatment Strategies for Castration-Resistant Prostate Cancer", Korean Journal of Urology, vol. 52, No. 3, Mar. 1, 2011, pp. 157-165.
Klein et al., "Analyzing Survival Curves at a Fixed Point in Time", Statistics in Medicine, vol. 26, No. 24, Oct. 30, 2007, pp. 4505-4519.
Klijn et al., "Antiprogestins a New Form of Endocrine Therapy for Human Breast Cancer", Cancer Research, vol. 49, No. 11, Jun. 1, 1989, pp. 2851-2856.
Kondo et al., "A Case of Ectopic Adrenocorticotropic Hormone-Producing Pancreatic Neuroendocrine Tumor with Multiple Liver Metastases", Endocrine Journal, vol. 57, No. 3, Apr. 2010, pp. 229-236.
Koochekpour , "Androgen Receptor Signaling and Mutations in Prostate Cancer", Asian Journal of Andrology, vol. 12, No. 5, Sep. 2010, pp. 639-657.
Korean Patent Application No. 10-2014-7036405 , Notice of Decision to Grant, Mailed On Nov. 26, 2019, 5 pages.
Korean Patent Application No. 10-2014-7036405 , Office Action, Mailed On Aug. 1, 2019, 5 pages.
Korean Patent Application No. 10-2019-7031825, Notice of Decision to Grant, Mailed On Oct. 12, 2021, 2 pages.
Korean Patent Application No. 10-2019-7031825 , Office Action, Mailed On Sep. 1, 2021, 11 pages.
Korean Patent Application No. 10-2019-7031825 , Office Action, Mailed On Mar. 2, 2021, 6 pages.
Kriaucionis et al., "The Nuclear DNA Base 5-Hydroxymethylcytosine is Present in Brain and Enriched in Purkinje Neurons", Science, vol. 324, No. 5929, May 15, 2009, 5 pages.
Kroon et al., "The Development of Novel Glucocorticoid Receptor Antagonists: From Rational Chemical Design to Therapeutic Efficacy in Metabolic Disease Models", Pharmacological Research, vol. 168, No. 105588, Jun. 2021, 13 pages.
Kugita, "Studies on the Syntheses of Hydrogenated Quinolines and Isoquinolines as Analgesics", Pharmaceutical Bulletin, vol. 4, No. 1, Feb. 1956, pp. 29-34.
Lante et al., "Subchronic Glucocorticoid Receptor Inhibition Rescues Early Episodic Memory and Synaptic Plasticity Deficits in a Mouse Model of Alzheimer's Disease", Neuropsychopharmacology, vol. 40, No. 7, Jun. 2015, pp. 1772-1781.
Li et al., "High Level of Androgen Receptor is Associated with Aggressive Clinicopathologic Features and Decreased Biochemical Recurrence-Free Survival in Prostate: Cancer Patients Treated with Radical Prostatectomy", The American Journal of Surgical Pathology, vol. 28, No. 7, Jul. 2004, pp. 928-934.
Li et al., "Systemic Overexpression of the 11β-HSD1 Promotes Endoplasmic Reticulum Stress in Multiple Tissues and the Development of Metabolic Syndrome in Mice", Molecular Medicine Reports, vol. 16, No. 5, Nov. 2017, pp. 7738-7744.
Loi et al., "Definition of Clinically Distinct Molecular Subtypes in Estrogen Receptor-Positive Breast Carcinomas Through Genomic Grade", Journal of Clinical Oncology, vol. 25, No. 10, Apr. 1, 2007, pp. 1239-1246.
Loi et al., "Predicting Prognosis Using Molecular Profiling in Estrogen Receptor-Positive Breast Cancer Treated With Tamoxifen", BMC Genomics, vol. 9, No. 239, May 22, 2008, pp. 1-12.
Lotan et al., "Up-Regulation of MKK4, MKK6 and MKK7 During Prostate Cancer Progression: An Important Role for SAPK Signalling in Prostatic Neoplasia", The Journal of Pathology, vol. 212, No. 4, Aug. 2007, pp. 386-394.
Lucci et al., "Modification of Ceramide Metabolism Increases Cancer Cell Sensitivity to Cytotoxics". International Journal of Oncology, vol. 15, No. 3, Sep. 1999, pp. 541-546.
Ma et al., "IL-21 Activates Both Innate and Adaptive Immunity to Generate Potent Antitumor Responses that Require Perforin but Are Independent of IFN-Gamma", Journal of Immunology, vol. 171, No. 2, Jul. 15, 2003, pp. 608-615.
Macpherson et al., "Glucocorticoids Worsen Excitotoxin-Induced Expression of Pro-Infammatory Cytokines in Hippocampal Cultures", Experimental Neurology, vol. 194, No. 2, Aug. 2005, pp. 376-383.
Magee et al., "Construction of Cis- and Trans- Decahydroisoquinolines Via Heterogeneous Catalytic Hydrogenation", The Journal of Organic Chemistry, American Chemical Society, vol. 64, No. 7, Mar. 16, 1999, pp. 2549-2554.

(56) References Cited

OTHER PUBLICATIONS

Mahmood et al., "3D-QSAR Comfa, Comsia Studies on Pyrazolo-Fused Azadecalins Derivatives as Selective Glucocorticoid Receptor Antagonists", Pharma Science Monitor, vol. 3, No. 3, Jul. 2012, pp. 2027-2055.
Makarov et al., "Updated Nomogram to Predict Pathologic Stage of Prostate Cancer Given Prostate-Specific Antigen Level, Clinical Stage, and Biopsy Gleason Score (Partin Tables) Based on Cases from 2000 to 2005", Urology, vol. 69, No. 6, Jun. 2007, pp. 1095-1101.
Melhem et al., "Administration of Glucocorticoids to Ovarian Cancer Patients is Associated with Expression of the Anti-apoptotic Genes SGK1 and MKP1/DUSP1 in Ovarian Tissues", Clinical Cancer Research, vol. 15, No. 9, May 1, 2009, pp. 3196-3204.
Meyer et al., "The Selective Glucocorticoid Receptor Modulator Cort 113176 Reduces Neurodegeneration and Neuroinflammation in Wobbler Mice Spinal Cord", Neuroscience, vol. 384, Aug. 1, 2018, pp. 384-396.
Meyer et al., "The Selective Glucocorticoid Receptor Modulator CORT108297 Restores Faulty Hippocampal Parameters in Wobbler and Corticosterone-Treated Mice", The Journal of Steroid Biochemistry and Molecular Biology, vol. 143, Sep. 2014, pp. 40-48.
Mikosz et al., "Glucocorticoid Receptor-Mediated Protection from Apoptosis is Associated with Induction of the Serine/Threonine Survival Kinase Gene, sgk-1", The Journal of Biological Chemistry, vol. 276, No. 20, May 18, 2001, pp. 16649-16654.
Miljkovic et al., "Methylprednisolone Inhibits IFN-Y and IL-17 Expression and Production by Cells Infiltrating Central Nervous System in Experimental Autoimmune Encephalomyelitis", Journal of Neuroinflammation, vol. 6, No. 37, Dec. 11, 2009, pp. 1-10.
Minn et al., "Genes that Mediate Breast Cancer Metastasis to Lung", Nature, vol. 436, No. 7050, Jul. 28, 2005, pp. 518-524.
Mohler et al., "Androgen and Glucocorticoid Receptors in the Stroma and Epithelium of Prostatic Hyperplasia and Carcinoma", Clinical Cancer Research, vol. 2, No. 5, May 1996, pp. 889-895.
Moller et al., "Impact of New Technologies for Cellular Screening Along the Drug Value Chain", Drug Discovery Today, vol. 15, Nos. 9-10, May 2010, pp. 384-390.
Montgomery et al., "Impact of Baseline Corticosteroids on Survival and Steroid Androgens in Metastatic Castration-Resistant Prostate Cancer: Exploratory Analysis from COU-AA-301", European Urology, vol. 67, No. 5, 2014, 8 pages.
Moran et al., "The Glucocorticoid Receptor Mediates a Survival Signal in Human Mammary Epithelial Cells", Cancer Research, vol. 60, No. 4, Feb. 15, 2000, pp. 867-872.
Moses et al., "The Growing Applications of Click Chemistry", Chemical Society Reviews, vol. 36, No. 8, May 2007, pp. 1249-1262.
Mottet et al., "EAU Guidelines on Prostate Cancer. Part II: Treatment of Advanced, Relapsing, and Castration- Resistant Prostate Cancer", European Urology, vol. 59, Jan. 2011, pp. 572-583.
Munhoz et al., "Chronic Unpredictable Stress Exacerbates Lipopolysaccharide-Induced Activation of Nuclear Factor-kappaB in the Frontal Cortex and Hippocampus Via Glucocorticoid Secretion", The Journal of Neuroscience, vol. 26, No. 14, Apr. 2006, pp. 3813-3820.
Munster et al., "A Phase 1/2 Study of Relacorilant + Nab-Paclitaxel (Nab-Pac) in Patients (Pts) with Solid Tumors: The Dose-Finding Phase", Journal of Clinical Oncology, vol. 36, No. 15, May 20, 2018, 4 pages.
Munster et al., "A Phase 1/2 Study of Relacorilant + Nab-Paclitaxel in Patients with Solid Tumors: The Dose-Finding Phase", American Association for Cancer Research, 2018, 1 page.
Mexican Patent Application No. MX/A/2014/014239 , Notice of Decision to Grant, Mailed On Apr. 23, 2019, 2 pages.
Mexican Patent Application No. MX/A/2014/014239 , Office Action, Mailed On Apr. 15, 2015, 2 pages.
Mexican Patent Application No. MX/A/2014/014239 , Office Action, Mailed On Jan. 24, 2019, 3 pages.
Mexican Patent Application No. MX/A/2014/014239 , Office Action, Mailed On Oct. 30, 2018, 3 pages.
Mexican Patent Application No. MX/A/2016/006725 , Notice of Decision to Grant, Mailed On Jul. 15, 2019, 2 pages.
Mexican Patent Application No. MX/A/2016/006725 , Office Action, Mailed On Apr. 29, 2019, 3 pages.
Mexican Patent Application No. MX/A/2019/011543 , Notice of Allowance, Mailed On Oct. 25, 2022, 4 pages.
Mexican Patent Application No. MX/A/2019/011543 , Office Action, Mailed On Aug. 11, 2022, 5 pages.
Mexican Patent Application No. MX/A/2019/011543 , Office Action, Mailed On Jun. 14, 2022, 5 pages.
Mexican Patent Application No. MX/A/2019/011543 , Office Action, Mailed On Apr. 12, 2022, 8 pages.
Malaysian Patent Application No. PI2014003289 , "Substantive Examination Adverse Report", Mar. 30, 2018, 2 pages.
Niemeier et al., "Androgen Receptor in Breast Cancer: Expression in Estrogen Receptor-Positive Tumors and In Estrogen Receptor-Negative Tumors with Apocrine Differentiation", Modern Pathology, vol. 23, No. 2, Feb. 2010, pp. 205-212.
Norman et al., "Functional Glucocorticoid Receptor Modulates Pancreatic Carcinoma Growth Through an Autocrine Loop", Journal of Surgical Research, vol. 57, No. 1, Jul. 1994, pp. 33-38.
Novotny et al., "Cancer Therapy: New Targets for Chemotherapy", Hematology, vol. 8, No. 3, Jun. 2003, pp. 129-137.
New Zealand Patent Application No. 756852 , "First Examination Report", Jun. 18, 2024, 4 pages.
New Zealand Patent Application No. 756852 , "Second Examination Report", Sep. 27, 2024, 2 pages.
Ocana et al., "Preclinical Development of Molecular-Targeted Agents for Cancer", Nature Reviews Clinical Oncology Review, vol. 8, No. 4, Apr. 2011, pp. 200-209.
Ohlmann et al., "Novel Options for the Treatment of Castration-Resistant Prostate Cancer", World Journal of Urology, vol. 30, No. 4, Aug. 2012, pp. 495-503.
Orayj et al., "Patterns and Determinants of Prescribing for Parkinson's Disease: A Systematic Literature Review", Parkinson's Disease, Review Article ID 9237181, vol. 2019, Nov. 2019, pp. 1-40.
Pan et al., "Activation of the Glucocorticoid Receptor is Associated with Poor Prognosis in Estrogen Receptor-Negative Breast Cancer", Cancer Research, vol. 71, No. 20, Oct. 15, 2011, pp. 6360-6370.
Pan et al., "Identification of Glucocorticoid Receptor (GR) Signatures in Primary Human Breast Cancer: Association with Relapse-Free Survival Time", Poster Presented by S.D. Conzen as a Short Talk, presented at Nuclear Receptors: Signaling, Gene Regulation and Cancer, Keystone Symposia on Molecular and Cellular Biology, Mar. 25, 2010, 1 page.
Pang et al., "Dexamethasone Decreases Xenograft Response to Paclitaxel Through Inhibition of Tumor Cell Apoptosis", Cancer Biology & Therapy, vol. 5, No. 8, Aug. 2006, pp. 933-940.
Panigrahi et al., "Gelucire: A Versatile Polymer for Modified Release Drug Delivery System", Future Journal of Pharmaceutical Sciences, vol. 4, No. 1, Apr. 2018, pp. 102-108.
Patacchioli et al., "Adrenal Dysregulation in Amyotrophic Lateral Sclerosis", Journal of Endocrinological Investigation, vol. 26, No. 12, Dec. 2003, pp. 1-6.
International Patent Application No. PCT/US13/27720 , International Search Report and Written Opinion, Mailed On Jun. 17, 2013, 9 pages.
International Patent Application No. PCT/US2005/008049 , International Search Report and Written Opinion, Mailed On Jun. 15, 2005, 8 pages.
International Patent Application No. PCT/US2009/049273 , International Search Report and Written Opinion, Mailed On Aug. 14, 2009, 11 pages.
International Patent Application No. PCT/US2009/49273 , International Search Report and Written Opinion, Mailed On Aug. 14, 2009, 7 pages.
International Patent Application No. PCT/US2010/034382 , International Search Report and Written Opinion, Mailed On Jul. 9, 2010, 7 pages.
International Patent Application No. PCT/US2011/049408 , International Search Report and Written Opinion, Mailed On Jan. 30, 2012, 10 pages.

(56) References Cited

OTHER PUBLICATIONS

International Patent Application No. PCT/US2013/027150 , International Preliminary Report on Patentability, Mailed On Sep. 4, 2014, 7 pages.
International Patent Application No. PCT/US2013/027150, International Search Report and Written Opinion, Mailed On Apr. 29, 2013, 9 pages.
International Patent Application No. PCT/US2013/027720 , International Search Report and Written Opinion, Mailed On Jun. 17, 2013, 8 pages.
International Patent Application No. PCT/US2013/042732 , International Preliminary Report on Patentability, Mailed On Dec. 4, 2014, 6 pages.
International Patent Application No. PCT/US2013/042732 , International Search Report and Written Opinion, Mailed On Nov. 13, 2013, 8 pages.
International Patent Application No. PCT/US2014/066759 , International Preliminary Report on Patentability, Mailed On Jun. 9, 2016, 6 pages.
International Patent Application No. PCT/US2014/066759 , International Search Report and Written Opinion, Mailed On Feb. 6, 2015, 9 pages.
International Patent Application No. PCT/US2017/019948 , International Preliminary Report on Patentability, Mailed On Sep. 13, 2018, 6 pages.
International Patent Application No. PCT/US2017/019948 , International Search Report and Written Opinion, Mailed On May 25, 2017, 12 pages.
International Patent Application No. PCT/US2017/050812 , International Preliminary Report on Patentability, Mailed On Mar. 21, 2019, 12 pages.
International Patent Application No. PCT/US2017/050812 , International Search Report and Written Opinion, Mailed On Dec. 26, 2017, 17 pages.
International Patent Application No. PCT/US2018/025547 , International Preliminary Report on Patentability, Mailed On Oct. 10, 2019, 10 pages.
International Patent Application No. PCT/US2018/025547 , International Search Report and Written Opinion, Mailed On Aug. 9, 2018, 13 pages.
International Patent Application No. PCT/US2019/067108 , International Preliminary Report on Patentability, Mailed On Jul. 1, 2021, 7 pages.
International Patent Application No. PCT/US2019/067108 , International Search Report and Written Opinion, Mailed On Apr. 21, 2020, 15 pages.
International Patent Application No. PCT/US2023/078018 , International Preliminary Report on Patentability, Mailed On May 8, 2025, 8 pages.
International Patent Application No. PCT/US2023/078018 , International Search Report and the Written Opinion, Mailed On Feb. 23, 2024, 13 pages.
Peruvian Patent Application No. 2054-2014 , "Notice of Grant", Apr. 24, 2019, 10 pages.
Peruvian Patent Application No. 2054-2014 , Office Action, Mailed On Jan. 10, 2019, 10 pages.
Peeters et al., "Differential Effects of the New Glucocorticoid Receptor Antagonist ORG 34517 and RU486 (Mifepristone) on Glucocorticoid Receptor Nuclear Translocation in the AtT20 Cell Line", Annals of the New York Academy of Sciences, vol. 1148, No. 1, Dec. 2008, pp. 536-541.
Perini et al., "Effects of Carbarnazepine on Pituitary-Adrenal Function in Healthy Volunteers", The Journal of Clinical Endocrinology and Metabolism, vol. 74, No. 2, Feb. 1, 1992, pp. 406-412.
Petrov et al., "ALS Clinical Trials Review: 20 Years of Failure. Are we Any Closer to Registering a New Treatment?", Frontiers in Aging Neuroscience, vol. 9, No. 68, Mar. 2017, pp. 1-11.
Petrylak et al., "Evaluation of Prostate-Specific Antigen Declines for Surrogacy in Patients Treated on SWOG 99-16", Journal of the National Cancer Institute, vol. 98, No. 8, Apr. 19, 2006, pp. 516-521.
Philippines Patent Application No. 1-2014-502584 , Notice of Allowance, Mailed On Oct. 26, 2015, 1 page.
Philippines Patent Application No. 1-2014-502584 , Substantive Examination Report, Mailed On Jul. 27, 2015, 1 page.
Philippines Patent Application No. 1-2016-500968 , Notice of Allowance, Mailed On Aug. 19, 2019, 3 pages.
Philippines Patent Application No. 1-2016-500968 , Substantive Examination Report, Mailed On Aug. 17, 2018, 3 pages.
Philippines Patent Application No. 1-2016-500968 , Substantive Examination Report, Mailed On Feb. 7, 2019, 3 pages.
Philippines Patent Application No. 1-2019-502259 , Office Action, Mailed On Jul. 9, 2024, 5 pages.
Philippines Patent Application No. 1-2019-502259 , Office Action, Mailed On Aug. 17, 2023, 9 pages.
Pike et al., "Estrogens, Progestogens, Normal Breast Cell Proliferation, and Breast Cancer Risk", Epidemiologic Reviews, vol. 15, No. 1, Jan. 1, 1993, pp. 17-30.
Pomara et al., "Mifepristone (RU 486) for Alzheimer's Disease", Neurology, vol. 58, May 2002, pp. 1436-1437.
Pound et al., "Natural History of Progression after PSA Elevation Following Radical Prostatectomy", Journal of the American Medical Association, vol. 281, No. 17, May 5, 1999, pp. 1591-1597.
Pouton , "Formulation of Poorly Water-Soluble Drugs for Oral Administration: Physiochemical and Physiological Issues and the Lipid Formulation Classification System", European Journal of Pharmaceutical Sciences 29, Nos. 4-5, Nov. 2006, pp. 278-287.
Rakotomamonjy et al., "Brain-Derived Neurotrophic Factor is Required for the Neuroprotective Effect of Mifepristone on Immature Purkinje Cells in Cerebellar Slice Culture", International Journal of Molecular Sciences, vol. 20, No. 2, Jan. 12, 2019, pp. 1-9.
Ramsay , "Immune Checkpoint Blockade Immunotherapy to Activate Anti-Tumour T-Cell Immunity", British Journal of Haematology, vol. 162, No. 3, Aug. 2013, pp. 313-325.
Rauhala et al., "Dual-Specificity Phosphatase 1 and Serum/Glucocorticoid-Regulated Kinase are Downregulated in Prostate Cancer", International Journal of Cancer, vol. 117, No. 5, Dec. 10, 2005, pp. 738-745.
Reagan-Shaw et al., "Dose Translation from Animal to Human Studies Revisited", The FASEB Journal, vol. 22, Mar. 2007, pp. 659-661.
Rehn et al., "Antiinflammatory Action of Glucocorticoids-New Mechanisms for Old Drugs", The New England Journal of Medicine, vol. 353, No. 16, Oct. 20, 2005, pp. 1711-1723.
Ring et al., "Mechanisms of Tamoxifen Resistance", Endocrine-Related Cancer, vol. 11, No. 4, Dec. 2004, pp. 643-658.
Robinson et al., "Octahydrophenanthrene-2,7-diol Analogues as Dissociated Glucocorticoid Receptor Agonists: Discovery and Lead Exploration", Journal of Medicinal Chemistry, vol. 52, No. 6, Mar. 26, 2009, pp. 1731-1743.
Roozendaal et al., "The Cortisol Awakening Response in Amyotrophic Lateral Sclerosis is Blunted and Correlates with Clinical Status and Depressive Mood", Psychoneuroendocrinology, vol. 37, Jan. 2012, pp. 20-26.
Rosner et al., "Higher Tumor to Benign Ratio of the Androgen Receptor mRNA Expression Associates with Prostate Cancer Progression after Radical Prostatectomy", Urology, vol. 70, No. 6, Dec. 2007, pp. 1225-1229.
Russian Patent Application No. 2014152625 , Notice of Decision to Grant, Mailed On Sep. 1, 2017, 28 pages.
Russian Patent Application No. 2014152625 , Office Action, Mailed On Apr. 17, 2017, 16 pages.
Russian Patent Application No. 2016123449 , Notice of Decision to Grant, Mailed On Oct. 17, 2018, 27 pages.
Russian Patent Application No. 2016123449 , Office Action, Mailed On Jun. 19, 2018, 14 pages.
Russian Patent Application No. 2019129299 , Notice of Decision to Grant, Mailed On Apr. 18, 2022, 17 pages.
Russian Patent Application No. 2019129299 , Office Action, Mailed On Aug. 18, 2021, 18 pages.

(56) References Cited

OTHER PUBLICATIONS

Russian Patent Application No. 2019129299 , Office Action, Mailed On Jan. 12, 2022, 20 pages.
Russian Patent Application No. 2019129299 , Office Action, Mailed On Mar. 30, 2021, 21 pages.
Russian Patent Application No. 2021120817 , Notice of Decision to Grant, Mailed On May 19, 2022, 11 pages.
Sahoo et al., "Coordinate Expression of the PI3-Kinase Downstream Effectors Serum and Glucocorticoid- Induced Kinase (SGK-1) and Akt-1 in Human Breast Cancer", European Journal of Cancer, vol. 41, No. 17, Nov. 2005, pp. 2754-2759.
Sahu et al., "FoxA1 Specifies Unique Androgen and Glucocorticoid Receptor Binding Events in Prostate Cancer Cells", Cancer Research, vol. 73, No. 5, Mar. 2013, pp. 1570-1580.
Samadhiya et al., "Assessment of Therapeutic Response of Edaravone and Riluzole Combination Therapy in Amyotrophic Lateral Sclerosis Patients", Annals of Indian Academy of Neurology, vol. 25, No. 4, Jul.-Aug. 2022, pp. 692-697.
Sausville et al., "Contributions of Human Tumor Xenografts to Anticancer Drug Development", Cancer Research, vol. 66, No. 7, Apr. 2006, pp. 3351-3354.
Schenone et al., "Target Identification and Mechanism of Action in Chemical Biology and Drug Discovery", Nature Chemical Biology, vol. 9, No. 4, Mar. 18, 2013, pp. 232-240.
Scher et al., "Antitumour Activity of MDV3100 in Castration-Resistant Prostate Cancer: A Phase 1-2 Study", Lancet, vol. 375, No. 9724, Apr. 24, 2010, pp. 1437-1446.
Scher et al., "Biology of Progressive, Castration-Resistant Prostate Cancer: Directed Therapies Targeting the Androgen-Receptor Signaling Axis", Journal of Clinical Oncology, vol. 23, No. 32, Nov. 10, 2005, pp. 8253-8261.
Scher et al., "End Points and Outcomes in Castration-Resistant Prostate Cancer: From Clinical Trials to Clinical Practice", Journal of Clinical Oncology, vol. 29, No. 27, Sep. 20, 2011, pp. 3695-3704.
Schlossmacher et al., "Glucocorticoid Receptor-Mediated Apoptosis: Mechanisms of Resistance In Cancer Cells", Journal of Endocrinology, vol. 211, No. 1, May 20, 2011, pp. 17-25.
Schultz et al., "Heteroatom Directed Photoarylation. Synthetic Potential of the Heteroatom Oxygen", Journal of the American Chemical Society, vol. 100, No. 7, Mar. 29, 1978, pp. 2150-2162.
Schultz et al., "Studies Directed at a Synthesis of the Morphine Alkaloids. A Photochemical Approach", The Journal of Organic Chemistry, vol. 50, No. 2, Jan. 1985, pp. 217-231.
Segovia-Mendoza et al., "Antihormonal Agents as a Strategy to Improve the Effect of Chemo-Radiation in Cervical Cancer: In Vitro and in Vivo Study", BMC Cancer, vol. 15, No. 21, Jan. 27, 2015, pp. 1-11.
Seruga et al., "Drug Resistance in Metastatic Castration-Resistant Prostate Cancer", Nature Reviews Clinical Oncology, vol. 8, No. 1, Jan. 2011, pp. 12-23.
Singaporean Patent Application No. 11201407682T , Notice of Decision to Grant, Mailed On Feb. 15, 2017, 4 pages.
Singaporean Patent Application No. 11201604077W , Notice of Decision to Grant, Mailed On Apr. 11, 2019, 5 pages.
Singaporean Patent Application No. 11201807421T , Written Opinion, Mailed On Sep. 26, 2019, 7 pages.
Singaporean Patent Application No. 11201908790P , Further Written Opinion, Mailed On Nov. 15, 2021, 7 pages.
Singaporean Patent Application No. 11201908790P , Written Opinion, Mailed On Dec. 9, 2020, 8 pages.
Singaporean Patent Application No. 11202105770Y , Written Opinion, Mailed On Jul. 17, 2022, 8 pages.
Shanmugam et al., "Serum/Glucocorticoid-Induced Protein Kinase-1 Facilitates Androgen Receptor-Dependent Cell Survival", Cell Death Differ, vol. 14, No. 12, Oct. 12, 2007, pp. 2085-2094.
Sharma et al., "Cell Line-Based Platforms to Evaluate the Therapeutic Efficacy of Candidate Anticancer Agents", Nature Reviews Cancer, vol. 10, No. 4, Apr. 2010, pp. 241-253.
Sherk et al., "Development of a Small Molecule Serum and Glucocorticoid-Regulated Kinase 1 Antagonist and its Evaluation as a Prostate Cancer Therapeutic", Cancer Research, vol. 68, No. 18, Sep. 15, 2008, pp. 7475-7483.
Sims et al., "The Removal of Multiplicative, Systematic Bias Allows Integration of Breast Cancer Gene Expression Datasets - Improving Meta-Analysis and Prediction of Prognosis", BMC Medical Genomics, vol. 1, No. 42, Sep. 21, 2008, pp. 1-14.
Skor et al., "Glucocorticoid Receptor Antagonism as a Novel Therapy for Triple-Negative Breast Cancer", Clinical Cancer Research, vol. 19, No. 22, Nov. 15, 2013, pp. 6163-6172.
Smith et al., "Expression of Glucocorticoid and Progesterone Nuclear Receptor Genes in Archival Breast Cancer Tissue", Breast Cancer Research, vol. 5, No. 1, 2003, pp. R9-R12.
Smith et al., "Progesterone, Glucocorticoid, but Not Estrogen Receptor mRNA is Altered in Breast Cancer Stroma", Cancer Letters, vol. 255, No. 1, Sep. 18, 2007, pp. 77-84.
Song et al., "Dihydrotestosterone Enhances Castration-Resistant Prostate Cancer Cell Proliferation through STAT5 Activation via Glucocorticoid Receptor Pathway", The Prostate, vol. 74, No. 12, Sep. 2014, pp. 1240-1248.
Sorlie et al., "Gene Expression Patterns of Breast Carcinomas Distinguish Tumor Subclasses with Clinical Implications", Proceedings of the National Academy of Sciences of the United States of America, vol. 98, No. 19, Sep. 11, 2001, pp. 10869-10874.
Sotiriou et al., "Gene Expression Profiling in Breast Cancer: Understanding the Molecular Basis of Histologic Grade to Improve Prognosis", Journal of the National Cancer Institute, vol. 98, No. 4, Feb. 15, 2006, pp. 262-272.
Spataro et al., "Plasma Cortisol Level in Amyotrophic Lateral Sclerosis", Journal of the Neurological Sciences, vol. 358, Nov. 2015, pp. 282-286.
Spitz et al., "Mifepristone (RU 486)—A Modulator of Progestin and Glucocorticoid Action", The New England Journal of Medicine, Massachusetts Medical Society, vol. 329, No. 6, Aug. 5, 1993, pp. 404-412.
Srinivas et al., "Phase II Study Evaluating Oral Triamcinolone in Patients with Androgen-Independent Prostate Cancer", Adult Urology, vol. 67, No. 5, May 1, 2006, pp. 1001-1006.
Srinivas et al., "Proteomics for Cancer Biomarker Discovery", Clinical Chemistry, vol. 48, No. 8, Aug. 2002, pp. 1160-1169.
Stephenson et al., "Preoperative Nomogram Predicting the 10-Year Probability of Prostate Cancer Recurrence After Radical Prostatectomy", Journal of the National Cancer Institute, vol. 98, No. 10, May 17, 2006, pp. 715-717.
Sterbis et al., "Higher Expression of the Androgen-Regulated Gene PSA/HK3 mRNA in Prostate Cancer Tissues Predicts Biochemical Recurrence-Free Survival", Clinical Cancer Research, vol. 14, No. 3, Feb. 2008, pp. 758-763.
Stringer-Reasor et al., "Glucocorticoid Receptor Activation Inhibits Chemotherapy-Induced Cell Death in High-Grade Serous Ovarian Carcinoma", Gynecologic Oncology, vol. 138, No. 3, Sep. 2015, pp. 656-662.
Sui et al., "Estrogen Receptor a Mediates Breast Cancer Cell Resistance to Paclitaxel Through Inhibition of Apoptotic Cell Death", Cancer Research, vol. 67, No. 11, Jun. 1, 2007, pp. 5337-5344.
Sun et al., "Castration Resistance in Human Prostate Cancer is Conferred by a Frequently Occurring Androgen Receptor Splice Variant", Journal of Clinical Investigation, vol. 120, No. 8, Aug. 2, 2010, pp. 2715-2730.
Sundahl et al., "Selective Glucocorticoid Receptor-Activating Adjuvant Therapy in Cancer Treatments", Oncoscience, vol. 3, Nos. 7-8, Jul. 2016, pp. 188-202.
Szmulewitz et al., "Serum/Glucocorticoid-Regulated Kinase 1 Expression in Primary Human Prostate Cancers", Prostate, vol. 72, No. 2, Feb. 1, 2012, pp. 157-164.
Tannock et al., "Docetaxel Plus Prednisone or Mitoxantrone Plus Prednisone for Advanced Prostate Cancer", The New England Journal of Medicine, vol. 351, No. 15, Oct. 7, 2004, pp. 1502-1512.

(56) References Cited

OTHER PUBLICATIONS

Taplin et al., "A Phase II Study of Mifepristone (RU-486) in Castration-Resistant Prostate Cancer, with a Correlative Assessment of Androgen-Related Hormones", BJU International, vol. 101, No. 9, May 1, 2008, pp. 1084-1089.
Tessier et al., "Serum and Glucocorticoid-Regulated Protein Kinases: Variations on a Theme", Journal of Cellular Biochemistry, vol. 98, No. 6, Aug. 15, 2006, pp. 1391-1407.
Tokuda et al., "Prednisolone (30-60 Mg/Day) for Diseases Other than AD Decreases Amyloid B-peptides in CSF", Neurology, vol. 58, No. 9, May 14, 2002, 1 page.
Touat et al., "Successful Treatment of Multiple Intracranial Meningiomas with the Antiprogesterone Receptor Agent Mifepristone (RU486)", Acta Neurochirurgica, vol. 156, No. 10, Oct. 2014, pp. 1831-1835.
Twiddy et al., "Cholesterol as a Potential Target for Castration-Resistant Prostate Cancer", Pharmaceutical Research, vol. 28, No. 3, Mar. 2011, pp. 423-437.
Ukrainian Patent Application No. A201909792 , Notice of Allowance, Mailed On May 22, 2023, 3 pages.
Ukrainian Patent Application No. A201909792 , Office Action, Mailed On Mar. 27, 2023, 5 pages.
Ukrainian Patent Application No. A201909792 , Office Action, Mailed On Mar. 9, 2022, 6 pages.
Uchida et al., "An Efficient Access to the Optically Active Manzamine Tetracyclic Ring System", Tetrahedron Letters, vol. 40, No. 1, Jan. 1, 1999, pp. 113-116.
Venkatesh et al., "Role of the Development Scientist in Compound Lead Selection and Optimization", Journal of Pharmaceutical Sciences, vol. 89, No. 2, Feb. 2000, pp. 145-154.
Von Hoff et al., "Increased Survival in Pancreatic Cancer with Nab-Paclitaxel Plus Gemcitabine", The New England Journal of Medicine, vol. 369, No. 18, Oct. 31, 2013, pp. 1691-1703.
Wang et al., "Gene-Expression Profiles to Predict Distant Metastasis of Lymph-Node-Negative Primary Breast Cancer", The Lancet, vol. 365, No. 9460, Feb. 19, 2005, pp. 671-679.
Ward et al., "Rising Prostate-Specific Antigen after Primary Prostate Cancer Therapy", Nature Clinical Practice Urology, vol. 2, No. 4, Apr. 1, 2005, pp. 174-182.
West et al., "Abstract PD3-02: Second-Generation Selective Glucocorticoid Receptor Modulators in Triple-Negative Breast Cancer", Cancer Research, vol. 76, No. 4, Feb. 15, 2016, 2 pages.
Wright et al., "Differences in Prostate Cancer Outcomes Between Cases With Gleason 4+3 and Gleason 3+4 Tumors in a Population-Based Cohort", The Journal of Urology, vol. 182, No. 6, Dec. 2009, pp. 2702-2707.
Wu et al., "Glucocorticoid Receptor Activation Signals Through Forkhead Transcription Factor 3a in Breast Cancer Cells", Molecular Endocrinology, vol. 20, No. 10, Oct. 1, 2006, pp. 2304-2314.
Wu et al., "Microarray Analysis Reveals Glucocorticoid-Regulated Survival Genes that are Associated with Inhibition of Apoptosis in Breast Epithelial Cells", Cancer Research, vol. 64, No. 5, Mar. 1, 2004, pp. 1757-1764.
Wu et al., "Prevalent Expression of the Immunostimulatory MHC Class I Chain-Related Molecule is Counteracted by Shedding in Prostate Cancer", Journal of Clinical Investigation, vol. 114, No. 4, Aug. 16, 2004, pp. 560-568.
Wymer et al., "Pharmacokinetics, Bioavailability, and Swallowing Safety with Riluzole Oral Film", Clinical Pharmacology in Drug Development, vol. 12, No. 1, Sep. 27, 2022, pp. 57-64.
Xie et al., "The Expression of Glucocorticoid Receptor is Negatively Regulated by Active Androgen Receptor Signaling in Prostate Tumors", International Journal of Cancer, vol. 136, Feb. 15, 2015, pp. E27-E38.
Yan et al., "Relationship between Glucocorticoid Receptor Signal Pathway and Androgen-Independent Prostate Cancer", Urologia Internationalis, vol. 81, No. 2, Aug. 29, 2008, pp. 228-233.
Yemelyanov et al., "Differential Targeting of Androgen and Glucocorticoid Receptors Induces ER Stress and Apoptosis in Prostate Cancer Cells", Cell Cycle, vol. 11, No. 2, Jan. 15, 2012, pp. 395-406.
Yemelyanov et al., "Tumor Suppressor Activity of Glucocorticoid Receptor in the Prostate", Oncogene, vol. 26, No. 13, Mar. 22, 2007, pp. 1885-1896.
Yu et al., "Systems Pharmacology of Mifepristone (RU486) Reveals its 47 Hub Targets and Network: Comprehensive Analysis and Pharmacological Focus on FAK-Src-Paxillin complex", Scientific Reports, vol. 5, No. 7830, Jan. 19, 2015, pp. 1-10.
South African Patent Application No. 2016/04026 , Notice of Allowance, Mailed On Feb. 14, 2019, 3 pages.
South African Patent Application No. 2016/04026 , Notice of Decision to Grant, Mailed On Mar. 27, 2019,.
South African Patent Application No. 2019/05736 , Notice of Allowance, Mailed On Sep. 2, 2022, 2 pages.
Zegarra-Moro et al., "Disruption of Androgen Receptor Function Inhibits Proliferation of Androgen- Refractory Prostate Cancer Cells", Cancer Research, vol. 62, No. 4, Feb. 15, 2002, pp. 1008-1013.
Zhang et al., "Corticosteroid Co-Treatment Induces Resistance to Chemotherapy in Surgical Resections, Xenografts and Established Cell Lines of Pancreatic Cancer", BMC Cancer, vol. 6, No. 61, Mar. 15, 2006, pp. 1-14.
Zhang et al., "Corticosteroids Induce Chemotherapy Resistance in The Majority of Tumour Cells From Bone, Brain, Breast, Cervix, Melanoma and Neuroblastoma", International Journal of Oncology, vol. 29, No. 5, Nov. 2006, pp. 1295-1301.
Zhao et al., "Glucocorticoid Receptor in Prostate Epithelia is not required for Corticosteroid-Induced Epithelial Hyperproliferation in the Mouse Prostate", The Prostate, vol. 74, May 23, 2014, pp. 1068-1078.
Zou et al., "Androgen-Induced Coactivator ANCCA Mediates Specific Androgen Receptor Signaling in Prostate Cancer", Cancer Research, vol. 69, No. 8, Apr. 2009, pp. 3339-3346.

* cited by examiner

CONCOMITANT ADMINISTRATION OF GLUCOCORTICOID RECEPTOR MODULATOR RELACORILANT AND PACLITAXEL, A DUAL SUBSTRATE OF CYP2C8 AND CYP3A4

CROSS-REFERENCE TO RELATED APPLICATION

This application is a continuation of U.S. patent application Ser. No. 17/672,380, filed Feb. 15, 2022, which is a continuation of U.S. patent application Ser. No. 17/331,130, filed May 26, 2021, now U.S. Pat. No. 11,285,145, which claims priority to and the benefit of, U.S. Provisional Patent Application No. 63/030,800, filed May 27, 2020. These applications are incorporated by reference in their entirety.

BACKGROUND

The simultaneous, or nearly simultaneous (e.g., concomitant) presence of two drugs in a subject may alter the effects of one or the other, or both, drugs. Such alterations are termed drug-drug interactions (DDIs). For example, the required dose of a drug is often strongly affected by the amount and rate of its degradation in, and elimination from, the body (e.g., by liver or kidney action). However, the presence of a second drug in the body, which is also being acted upon, e.g., by the liver and kidney, can have significant effects on the amount and rate of degradation of the first drug, and can increase or decrease the amount of the first drug that remains in the body at a given time as compared to the amount that would have been present at that time in the absence of the second drug. Thus, for example, the presence of a second drug that is an inhibitor of an enzyme that metabolizes a first drug will inhibit the metabolism of the first drug and thus can often increase the effective dose of the first drug. Where the first drug has toxic side effects, such an increase in effective dose of the first drug may lead to dangerous toxicity that would not have been expected were the second drug not present.

Concomitant administration of different drugs often leads to adverse effects since the metabolism and/or elimination of each drug may reduce or interfere with the metabolism and/or elimination of the other drug(s), thus altering the effective concentrations of those drugs as compared to the effective concentrations of those drugs when administered alone. Thus, concomitant administration of drugs may increase the risk of toxic effects of one or both of the co-administered drugs.

Cytochrome P450 (abbreviated as CYP or P450) enzymes are hemoproteins of approximately 500 amino acids. Fifty-seven human functional CYP genes have been identified. The human CYP genes are classified into 18 families, designated by a Roman numeral, and 44 subfamilies designated by a capital letter. Classification is based on the amino acid sequence identity of the encoded proteins (Nelson, 2009). Eleven enzymes from CYP families 1, 2 and 3 (CYP1A1, CYP1A2, CYP2A6, CYP2B6, CYP2C8, CYP2C9, CYP2C19, CYP2D6, CYP2E1, CYP3A4 and CYP3A5) primarily contribute to drug and chemical metabolism (Guengerich 208; Zanger and Schwab 2013). These enzymes contribute to the biotransformation of approximately 70% of clinically used drugs. Generally, these enzymes provide a clearance mechanism for drugs and other xenobiotics and facilitate elimination from the body in urine and/or bile. CYP represents one of nature's most versatile enzymes with respect to its broad substrate profile and types of biotransformation reactions. The individual CYP enzymes exhibit distinct, but sometimes overlapping, substrate and inhibitor selectivities. Many drugs inhibit the activity of one or more CYP enzymes, and thus have the potential to cause a drug-drug interaction. Thus, a therapeutic dose of a first drug that is metabolized by a CYP enzyme may become a toxic dose when the first drug is administered with a second drug that inhibits that same CYP enzyme, since the CYP enzyme action on the first drug will be reduced by the presence of the second drug, leading to increased levels of the first drug (as compared to the levels obtained by the same dose of the first drug in the absence of the second drug).

Many therapeutically important drugs are metabolized by the CYP enzymes. CYP2C8 substrate drugs include amodiaquine, cerivastatin, dasabuvir, enzalutamide, imatinib, loperamide, montelukast, paclitaxel, pioglitazone, repaglinide, and rosiglitazone (Beckman et al., Pharmacol Rev 68:168-241 (2016)). DDIs between CYP2C8 substrates and other drugs can be significant; Gibbons et al. recommended reducing the dose of enzalutamide to about half the single-agent dose during concomitant use with a potent CYP2C8 inhibitor (Clin Pharmacokinet (2015) 54:1057-1069). Substrates metabolized by CYP3A4 include, for example, midazolam, triazolam, and paclitaxel. Paclitaxel (taxol) is widely used as a chemotherapeutic agent to treat a variety of types of cancer including ovarian, breast, prostate, esophageal, melanoma, and other solid tumor cancers. The primary route of elimination of paclitaxel is through metabolism by both CYP3A4 and CYP2C8. Drug-drug interactions with clopidogrel (a potent CYP2C8 inhibitor) can reduce paclitaxel clearance, leading to increased risk of paclitaxel toxicity, so that "[c]aution should be exercised whenever the simultaneous use of paclitaxel and clopidogrel cannot be avoided" (Bergman et al., Br J Clin Pharmacol (2015) 81(2):313-315). The label for paclitaxel includes a warning that caution should be exercised when paclitaxel is co-administered with a CYP2C8 and/or CYP3A4 inhibitor. Nab-paclitaxel is an albumin bound form of paclitaxel that is associated with fewer side-effects than paclitaxel.

Relacorilant (see FIG. 1; see also Hunt et al., J. Med. Chem. 60:3405-3421 (2017)) is a selective, non-steroidal modulator of the glucocorticoid receptor that is being investigated in clinical trials in patients with Cushing's syndrome and in patients with various types of cancer including ovarian cancer and pancreatic cancer.

SUMMARY

Many therapeutic drugs are substrates of CYP2C8 enzymes, CYP3A4 enzymes, or both; an otherwise safe dose of a first drug metabolized by these CYP enzymes may be a toxic dose when concomitantly administered with a second drug that is an inhibitor of the CYP enzyme. Where a therapeutic drug's primary route of elimination is through metabolism by both CYP2C8 and CYP3A4 enzymes, administration of a concomitant drug that inhibits of both CYP2C8 and CYP3A4 would be expected to cause a substantial increase in the plasma levels of the therapeutic drug by blocking its only elimination pathways. Co-administration with a dual inhibitor of CYP2C8 and CYP3A4 would lead to a greater magnitude of drug-drug interactions (DDIs) versus co-administration with an inhibitor of only one of the enzymes. In vitro studies are used to indicate drug combinations expected to suffer from such negative DDIs.

Relacorilant is believed to be useful in treating many disorders, including cancer and hypercortisolism. Relacorilant is further believed to be useful in combination treatments for cancer and in treating hypercortisolism. In vitro tests demonstrated that relacorilant is a potent inhibitor of CYP2C8 ($IC_{50}$ of 0.21 μM) and a potent inhibitor of CYP3A4 ($IC_{50}$ of 1.32 μM). Such potent dual inhibition of both CYP2C8 and CYP3A4 would be expected to increase plasma exposure of dual CYP2C8 and CYP3A4 substrates by more than five-fold when co-administered with relacorilant. Thus, it was expected that significant reductions in doses of dual CYP2C8 and CYP3A4 substrates (e.g., paclitaxel) would be required when administered in combination with relacorilant.

Upon co-administration with relacorilant such potent inhibition of both CYP2C8 and CYP3A4 by relacorilant would be expected to increase plasma exposure of paclitaxel by blocking its primary pathway of elimination through CYP2C8- and CYP3A4-mediated metabolism. Thus, it was expected that significant reductions in paclitaxel dose would be required when administered in combination with relacorilant. On the basis of relacorilant's expected effect on paclitaxel metabolism, co-administration of paclitaxel and relacorilant would have been expected to require potential reductions in paclitaxel dose by 5-fold or more when paclitaxel is administered with relacorilant.

Surprisingly, Applicant has discovered that co-administration of paclitaxel and relacorilant does not require such significant reductions in paclitaxel dose. Applicant has discovered that the plasma levels of paclitaxel are not increased by 5-fold or more, but are surprisingly only increased by about 80% (compared to the plasma levels when the same dose of paclitaxel is administered alone) when co-administered with relacorilant.

Thus, based on in vitro potent, dual inhibition of both CYP2C8 and CYP3A4, a significant increase of 5-fold or more in paclitaxel exposure is expected when paclitaxel is administered concomitantly with relacorilant. Surprisingly, Applicant discloses herein that relacorilant and paclitaxel may be concomitantly administered with only a small reduction in the dose of paclitaxel. Accordingly, in contrast to the expected requirement of reductions in paclitaxel dose by 5-fold or more, Applicant discloses herein that relacorilant may be safely administered along with paclitaxel, where the dose of paclitaxel is reduced by about 20% to about 35% (e.g., by about 20%, or by about 25%, or by about 30%, or by about 35%) as compared to the paclitaxel dose that is administered in the absence of relacorilant (typically about 100-125 mg/$m^2$). Applicant discloses herein that relacorilant may be safely administered along with paclitaxel, where the dose of paclitaxel is reduced to about 80 mg/$m^2$ (e.g., to about 65 mg mg/$m^2$, or about 70 mg/$m^2$, or about 75 mg/$m^2$, or about 80 mg/$m^2$, or about 85 mg/$m^2$, or about 90 mg/$m^2$, or about 95 mg/$m^2$) from the paclitaxel dose that is administered in the absence of relacorilant (typically about 100-125 mg/$m^2$). In embodiments, paclitaxel is administered in the form of nab-paclitaxel. Such concomitant administration of paclitaxel and relacorilant is believed to be safe for the subject and to provide the therapeutic benefits of both drugs to the subject.

The methods disclosed herein surprisingly provide safe methods for administering drug combinations and dosages that were previously expected to be unsafe, allowing safe and effective concomitant administration of paclitaxel with relacorilant. Such drug combinations are believed to provide more effective treatments than treatment with only one of the drugs in the absence of the other. The surprising ability to safely administer these drug combinations provides advantages including more effective treatments, absence of previously expected side effects, and other advantages.

BRIEF DESCRIPTION OF THE DRAWING

FIG. 1 shows the chemical structure of relacorilant ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridine-2-yl)methanone).

DETAILED DESCRIPTION

Based on the results of standard in vitro testing, relacorilant was found to be a potent inhibitor of CYP2C8 and of CYP3A4. These in vitro results indicated that co-administration of relacorilant would increase the plasma levels of a CYP2C8 and/or CYP3A4 substrate by greater than 5-fold. Paclitaxel is a substrate for both CYP2C8 and CYP3A4 metabolism. For this reason, co-administration of relacorilant and paclitaxel would thus be expected to greatly increase the concentration of paclitaxel above that concentration obtained when paclitaxel alone was administered. Similar to the in vitro results, human clinical studies showed an 8-fold increase in the exposure of midazolam (a standard CYP3A4 substrate) when concomitantly administered with relacorilant. Surprisingly, in human clinical studies conducted in healthy volunteers to evaluate the effect of relacorilant on the concentration of pioglitazone (a standard CYP2C8 substrate), no increase in the concentration of pioglitazone was observed. Also surprisingly, human studies in cancer patients found that co-administration of paclitaxel and relacorilant increased paclitaxel plasma levels only by about 80%, instead of the expected greater increases predicted by the in vitro potent, dual inhibition of both CYP2C8 and CYP3A4.

Applicant discloses herein the surprising discovery that relacorilant may be safely co-administered with paclitaxel with minor dose adjustments. Such small dose adjustments are surprisingly smaller than would be expected based on the greater increases predicted by the in vitro potent, dual inhibition of both CYP2C8 and CYP3A4. In embodiments, relacorilant and paclitaxel may be co-administered to a patient in need of treatment, by reducing the paclitaxel dose to about 80 mg/$m^2$, from a paclitaxel dose of about 100 mg/$m^2$ to about 125 mg/$m^2$ that is required for treatment by paclitaxel alone. Relacorilant and paclitaxel may be co-administered to treat cancer, such as ovarian or pancreatic cancer, by reducing the paclitaxel dose to about 80 mg/$m^2$, from a paclitaxel dose of about 100 mg/$m^2$ to about 125 mg/$m^2$ that is required for cancer treatment by paclitaxel alone. Such co-administration of relacorilant and paclitaxel provides therapeutically effective levels of both relacorilant and of paclitaxel at the same time in the patient, while avoiding excessive or toxic doses of either drug.

In embodiments, Applicant discloses a method of treating cancer, comprising administering to a patient in need of treatment for said cancer:

a) an effective dose of relacorilant; and b) an effective dose of paclitaxel, wherein said paclitaxel has a single agent dose of about 100 mg/$m^2$ to about 125 mg/$m^2$ when administered without other pharmaceutical agents, wherein said effective dose of paclitaxel is reduced by about 20% to about 35% from said single agent dose of paclitaxel when co-administered with relacorilant;

Wherein a) and b) are performed at times effective to provide the patient with an effective level of relacorilant and an effective level of paclitaxel at the same time, Whereby the cancer is treated.

In embodiments, the effective dose of paclitaxel is reduced by about 20%, or by about 25%, or by about 30%, or by about 35%, from said single agent dose of paclitaxel when co-administered with relacorilant. For example, when co-administered with relacorilant, where the effective dose of paclitaxel is a single agent dose of about 100 mg/m$^2$, the reduced paclitaxel dose may be reduced by about 20% to be about 80 mg/m$^2$. Where the effective dose of paclitaxel is a single agent dose of about 110 mg/m$^2$, the reduced paclitaxel dose when co-administered with relacorilant may be reduced by about 20% to be about 88 mg/m$^2$. Where the effective dose of paclitaxel is a single agent dose of about 120 mg/m$^2$, the reduced paclitaxel dose when co-administered with relacorilant may be reduced by about 20% to be about 96 mg/m$^2$. Where the effective dose of paclitaxel is a single agent dose of about 125 mg/m$^2$, the reduced paclitaxel dose when co-administered with relacorilant may be reduced by about 20% to be about 100 mg/m$^2$. For further example, where the reduced paclitaxel dose may be reduced by about 25% when co-administered with relacorilant, a single agent dose of paclitaxel of about 100 mg/m$^2$ would be reduced to be about 75 mg/m$^2$; a single agent dose of paclitaxel of about 110 mg/m$^2$ would be reduced to be about 83 mg/m$^2$; a single agent dose of paclitaxel of about 120 mg/m$^2$ would be reduced to be about 90 mg/m$^2$; and a single agent dose of paclitaxel of about 125 mg/m$^2$ would be reduced to be about 94 mg/m$^2$. Where the paclitaxel dose may be reduced by about 30% when co-administered with relacorilant, a single agent dose of paclitaxel of about 100 mg/m$^2$ would be reduced to be about 70 mg/m$^2$; a single agent dose of paclitaxel of about 110 mg/m$^2$ would be reduced to be about 77 mg/m$^2$; a single agent dose of paclitaxel of about 120 mg/m$^2$ would be reduced to be about 84 mg/m$^2$; and a single agent dose of paclitaxel of about 125 mg/m$^2$ would be reduced to be about 88 mg/m$^2$. Where the paclitaxel dose may be reduced by about 35% when co-administered with relacorilant, a single agent dose of paclitaxel of about 100 mg/m$^2$ would be reduced to be about 65 mg/m$^2$; a single agent dose of paclitaxel of about 110 mg/m$^2$ would be reduced to be about 72 mg/m$^2$; a single agent dose of paclitaxel of about 120 mg/m$^2$ would be reduced to be about 78 mg/m$^2$; and a single agent dose of paclitaxel of about 125 mg/m$^2$ would be reduced to be about 81 mg/m$^2$. In embodiments, paclitaxel is administered in the form of nab-paclitaxel.

In embodiments, Applicant discloses a method of treating cancer, comprising administering to a patient in need of treatment for said cancer:

a) an effective dose of relacorilant; and b) an effective dose of paclitaxel, wherein said paclitaxel has a single agent dose of about 100 mg/m$^2$ to about 125 mg/m$^2$ when administered without other pharmaceutical agents, wherein said effective dose of paclitaxel is between about 65 mg/m$^2$ to about 95 mg/m$^2$ when co-administered with relacorilant;

Wherein a) and b) are performed at times effective to provide the patient with an effective level of relacorilant and an effective level of paclitaxel at the same time, Whereby the cancer is treated.

In embodiments, the effective dose of paclitaxel is about 65 mg/m$^2$, or about 70 mg/m$^2$, or about 75 mg/m$^2$, or about 80 mg/m$^2$, or about 85 mg/m$^2$, or about 90 mg/m$^2$, or about 95 mg/m$^2$ when co-administered with relacorilant. In embodiments, the effective dose of paclitaxel is 80 mg/m$^2$ when co-administered with relacorilant. In embodiments, paclitaxel is administered in the form of nab-paclitaxel.

In embodiments, the cancer is ovarian cancer; or pancreatic cancer; or prostate, esophageal, melanoma, and or other solid tumor cancer.

Applicant's surprising discovery is believed to apply to patients suffering from a disease or disorder treatable by paclitaxel and by relacorilant, such as cancer. For example, patients receiving paclitaxel for the treatment of ovarian cancer or for pancreatic cancer may benefit from concomitant treatment with paclitaxel and relacorilant, and, while receiving relacorilant, may continue to receive paclitaxel by reducing the paclitaxel dose to about 80 mg/m$^2$ from a paclitaxel dose of about 100 mg/m$^2$ to about 125 mg/m$^2$ (the paclitaxel dose required for treatment by paclitaxel alone).

In embodiments, relacorilant is administered orally. In embodiments, relacorilant, is administered on a daily basis; for example, in embodiments, relacorilant is administered once per day. In embodiments, relacorilant is administered with food. Administered "with food" means that the patient has begun eating a meal within 30 minutes, or within one hour, of the time that relacorilant is administered. For example, relacorilant may be administered to a patient with a meal, or soon after (e.g., within half an hour) the patient began eating the meal.

In alternative embodiments, relacorilant is administered to a fasted patient, i.e., to a patient who has not eaten food for at least one hour, or at least two hours, or more hours prior to relacorilant administration. For example, relacorilant may be administered to a fasted patient in the morning, i.e., to a patient who has not yet eaten the morning meal, and has not eaten since the evening meal of the prior evening.

In embodiments, relacorilant is administered daily, at a daily dose of relacorilant of between about 1 and 100 mg/kg/day, preferably a daily dose of relacorilant of between about 1 and 20 mg/kg/day. In embodiments, the daily dose of relacorilant is between about 10 and about 2000 milligrams (mg), or between about 50 and about 1500 mg, or between about 100 and about 1000 mg relacorilant. In embodiments, a daily dose of relacorilant may be about 10 mg, or 15 mg, or 20 mg, or 25 mg, or 50 mg, or 100 mg, or 150 mg, or 200 mg, or 250 mg, or 300 mg, or 350 mg, or 400 mg, or 450 mg, or 500 mg, or 550 mg, or 600 mg, or 650 mg, or 700 mg, or 750 mg, of 800 mg, or 850 mg, or 900 mg, or 950 mg of relacorilant. In embodiments, an effective dose of relacorilant is between 75 milligrams per day (mg/day) and 200 mg/day, and may be selected from 75 mg/day, 100 mg/day, 125 mg/day, 150 mg/day, 175 mg/day, and 200 mg per day. In embodiments, the effective dose of relacorilant is 100 mg/day, 125 mg/day, or 150 mg/day. In embodiments, the effective dose of relacorilant is 100 mg/day, 125 mg/day, or 150 mg/day. In embodiments, the relacorilant dose may be adjusted (e.g., increased) from an initial dose during the course of treatment.

In embodiments, paclitaxel is administered as nab-paclitaxel. In embodiments, the dose of nab-paclitaxel is about 60 to about 95 mg/m$^2$, e.g., about 70 to 90 mg/m$^2$, and may be administered by intravenous infusion. For example, nab-paclitaxel may be administered at a dose of 80 mg/m$^2$ administered by intravenous (iv) infusion. Such infusions may be administered intermittently. For example, such infusions may be administered on days 1, 8 and 15 of each 28-day cycle. In embodiments, the dose of nab-paclitaxel is 60 mg/m$^2$ administered by iv infusion on days 1, 8 and 15 of each 28-day cycle. In embodiments, relacorilant is administered every day. In embodiments, relacorilant may be administered at a dose of between about 75 to about 250 mg, e.g., at a dose of 100 mg, or 125 mg, or 150 mg, or 175 mg, or 200 mg. In embodiments, relacorilant is administered every day at a dose of 100 mg. In embodiments, relacorilant is administered every day at a dose of 150 mg. In embodiments, e.g., wherein paclitaxel is nab-paclitaxel, relacorilant is administered daily at a dose of 150 mg. In embodiments, e.g., wherein paclitaxel is nab-paclitaxel, relacorilant is administered daily at a dose of 200 mg. In embodiments, e.g., wherein paclitaxel is nab-paclitaxel, relacorilant is administered intermittently (the day before, the day of and the day after the nab-paclitaxel infusion) at a dose of 150 mg. In embodiments, e.g., wherein paclitaxel is nab-paclitaxel, relacorilant is administered intermittently (the day before, the day of and the day after the nab-paclitaxel infusion) at a dose of 200 mg.

Definitions

As used herein, the term "patient" refers to a human that is or will be receiving, or has received, medical care for a disease or condition.

As used herein, the terms "administer," "administering," "administered" or "administration" refer to providing a compound or a composition (e.g., one described herein), to a subject or patient. Administration may be by oral administration (i.e., the subject receives the compound or composition via the mouth, as a pill, capsule, liquid, or in other form suitable for administration via the mouth). Oral administration typically involves swallowing the pill, capsule, liquid, or other formulation. Oral administration may include buccal administration (where the compound or composition is held in the mouth, e.g., under the tongue, and absorbed there).

Other examples of modes of administration include, e.g., by injection, i.e., delivery of the compound or composition via a needle, microneedle, pressure injector, or other means of puncturing the skin or forcefully passing the compound or composition through the skin of the subject. Injection may be intravenous (i.e., into a vein); intraarterial (i.e., into an artery); intraperitoneal (i.e., into the peritoneum); intramuscular (i.e., into a muscle); or by other route of injection. Routes of administration may also include rectal, vaginal, transdermal, via the lungs (e.g., by inhalation), subcutaneous (e.g., by absorption into the skin from an implant containing the compound or composition), or by other route.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art.

As used herein, the terms "co-administration", "concomitant administration", "combined administration", "combination treatment", and the like refer to the administration of at least two pharmaceutical agents to a subject to treat a disease or condition. The two agents may be administered simultaneously, or sequentially in any order during the entire or portions of the treatment period. The at least two agents may be administered following the same or different dosing regimens. Such agents may include, for example, e.g., relacorilant and another drug, which may be, e.g., a drug useful in treating hypercortisolism, may be a drug useful in treating cancer, or another therapeutic agent. In some cases, one agent is administered following a scheduled regimen while the other agent is administered intermittently. In some cases, both agents are administered intermittently. In some embodiments, the one pharmaceutical agent may be administered daily, and the other pharmaceutical agent may be administered every two, three, or four days.

As used herein, the terms "intermittent" and "intermittently" refer to administration of doses of a pharmaceutical agent or compound ("drug") that is other than daily administration; for example, administration of a dose of a compound on alternate days is intermittent administration of the compound. Any schedule of administration less frequently than daily administration is intermittent administration; further examples of intermittent administration include, but are not limited to, e.g., be administration every two days, or every three, or every four days. Intermittent administration also includes, for further examples, administration of a first drug on the day before, the day of and the day after the administration of a second drug; administration of a first drug on day 1, day 15, and day 28 of a repeated cycle of drug administration, which may include administration of a second drug on a different schedule of administration; and other schedules and sequences of drug administration.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Therapeutic agents such as relacorilant, pioglitazone, rosiglitazone, enzalutamide, and others, are typically administered in capsules, tablets, or other formulations which include the active agent and one or more pharmaceutically acceptable carriers. The use of such media and agents for pharmaceutically active substances is well known in the art. Except insofar as any conventional media or agent is incompatible with the active compound, use thereof in the compositions is contemplated. Supplementary active agents can also be incorporated into the compositions.

The term "glucocorticoid receptor modulator" (GRM) refers to any compound which modulates GC binding to GR, or which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

Relacorilant (((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridine-2-yl) methanone)) is a GRM. Relacorilant is described in Example 18 of U.S. Pat. No. 8,859,774 (hereby incorporated by reference).

As used herein, the term "CYP2C8" refers to the cytochrome P450 enzyme subtype 2C8. In humans, the most common form has 490 amino acids, and has the UniProtKB accession number P10632.2. The gene encoding CYP2C8 has Gene ID 1558.

CYP2C8 substrate drugs include amodiaquine, cerivastatin, dasabuvir, enzalutamide, imatinib, loperamide, montelukast, paclitaxel, pioglitazone, repaglinide, and rosiglitazone (Beckman et al., Pharmacol Rev 68:168-241 (2016)).

As used herein, the term "CYP3A4" refers to the cytochrome P450 enzyme subtype 3A4. In humans, common isoforms have 503 amino acids (isoform 1) or 502 amino acids (isoform 2), and the protein has the UniProtKB accession number P10632.2. The gene encoding CYP3A4 has Gene ID 1576.

CYP3A4 substrate drugs include paclitaxel, midazolam and triazolam.

Example 1. In Vitro CYP Inhibition Assay

Cytochrome P450 (CYP) isoforms CYP2B6, CYP2C8 and CYP3A5, heterologously expressed in *E. coli*, were obtained from Cypex and mixed to produce a 3-CYP mix. In a separate assay, isoforms for CYP1A2, CYP2C9, CYP2C19, CYP2D6, and CYP3A4 heterologously expressed in *E. coli* and obtained from Cypex as a custom made mixture of 5 isoforms. A selective and FDA accepted substrate for each isoform was present in the reaction at a concentration around its $K_m$.

Relacorilant (final concentration range 0.032-10 μM, 1% DMSO) or a cocktail of control CYP inhibitors was added to reaction tubes in a 96 well plate format. The CYP mix and a CYP substrate cocktail were added and the tubes warmed for 3 minutes whilst mixing on a BioShake IQ (37° C., 1500 rpm). NADPH (final concentration 1 mM) was added and the mixture was incubated for 10 minutes. Methanol containing an internal standard (1 μM tolbutamide) was then added to all samples, and these were mixed and placed at −20° C. for ≥1 hour to quench the reaction and allow protein to precipitate.

All samples were centrifuged (2500×g, 20 minutes, 4° C.). The supernatants were transferred to a fresh 96 well plate, compatible with an autosampler. The plate was sealed with a pre-slit silicone mat and the metabolites were analyzed by LC-MS/MS.

Control CYP inhibitors ($IC_{50}$—appropriate concentration range, final assay concentration 1% DMSO) were added as a cocktail. In Assay 1, the cocktail consisted of CYP2B6, ticlopidine; CYP2C8, quercetin; CYP3A5, ketoconazole. In Assay 1, the cocktail consisted of CYP1A2, α-naphthoflavone; CYP2C9, sulfaphenazole; CYP2C19, tranylcypromine; CYP2D6, quinidine; CYP3A4, ketoconazole.

In Assay 1, the final concentration of the 3-CYP mix was 18 pmol/mL for CYP2B6 (where pmol is picomoles), 1 pmol/mL for CYP2C and 5 pmol/mL for CYP3A5. In Assay 2, the final concentration of the 5-CYP mix was 32.5 pmol/ml for each of the enzymes evaluated (i.e., CYP1A2, CYP2C9, CYP2C19, CYP2D6, and CYP3A4). In Assay 1, the CYP substrate cocktail comprised the following components: CYP2B6, bupropion; CYP2C8, amodiaquine; CYP3A5, midazolam. The solvent was methanol for all stock solutions and the final concentration of methanol in the assay was 0.625%. The metabolites measured were: CYP2B6, hydroxybupropion; CYP2C8, N-desethyl amodiaquine; CYP3A5, 1'-hydroxymidazolam.

In Assay 2, the CYP substrate cocktail comprised the following components: CYP1A2, tacrine; CYP2C9, diclofenac; CYP2C19, (S)mephenytoin; CYP2D6, bufuralol; CYP3A4, midazolam. The metabolites measured were: CYP1A2, 1-hydroxytacrine; CYP2C9, 4'-hydroxydiclofenac; CYP2C19, 4'-hydroxymephenytoin; CYP2D6, hydroxybufuralol; CYP3A4, 1'-hydroxymidazolam.

All reactions were performed in duplicate at 37° C. and in 0.1 M phosphate buffer (pH 7.4). In Assay 1, the final protein concentration was 0.06 mg/ml. In Assay 2, the final protein concentration was 0.12 mg/ml.

Data Processing

Data were processed and the results reported as an $IC_{50}$ value (concentration resulting in a 50% inhibition of response), generated from a pseudo-Hill plot, the slope and y axis intercept being used to calculate the $IC_{50}$ according to the following equation.

$$IC_{50} = 10^{\frac{intercept}{slope}}$$

In Assay 1, relacorilant inhibited CYP2C8 with a mean $IC_{50}$ value of 0.21 μM in this assay. In Assay 2, relacorilant inhibited CYP3A4 with a mean $IC_{50}$ value of 1.32 μM.

Based on the in vitro data showing that relacorilant potently inhibited CYP2C8 with a mean $IC_{50}$ value of 0.21 μM, co-administration of a therapeutic concentration of relacorilant with a CYP28 substrate would be expected to result in a greater than 5-fold increase in the plasma exposure of the CYP2C8 substrate, relative to administration of the CYP2C8 substrate alone. Based on the in vitro CYP2C8 results, and based on the in vitro data showing that relacorilant potently inhibited CYP3CA4 with a mean $IC_{50}$ value of 1.32 μM, co-administration of a therapeutic concentration of relacorilant would be expected to increase the plasma exposure of dual CYP2C8 and CYP3A4 substrates by more than five-fold, relative to administration of the substrate alone.

Example 2. Clinical Drug-Drug Interaction Study in Healthy Volunteers

An open-label, crossover study was conducted in healthy subjects to determine the effect of relacorilant on the plasma exposure of midazolam, a known substrate of CYP3A4, and pioglitazone, a known substrate of CYP2C8. A single dose of midazolam 2.5 mg was administered alone and intensive pharmacokinetic (PK) samples were collected before dosing (0 hour) and at 0.25, 0.5, 1, 1.5, 2, 4, 6, 8, 12, 16, and 24 hours post-dose. On the following day, a single dose of 15 mg of pioglitazone was administered alone and intensive PK samples were collected before dosing (0 hour) and at 0.5, 1, 1.5, 2, 2.5, 3, 4, 6, 8, 12, 18, 24, 36, 48, 60, and 72 hours post-dose. Relacorilant 350 mg was then administered once a day for 9 consecutive days. On the tenth day of once-daily relacorilant dosing, a single dose of midazolam 2.5 mg was administered in combination with relacorilant 350 mg and intensive PK samples were again collected at pre-dose though 24 hours post-dose. On the following day, a single dose of 15 mg of pioglitazone was administered in combination with relacorilant 350 mg and intensive pharmacokinetic (PK) samples were again collected at pre-dose through 72 hours post-dose. The plasma concentrations of midazolam and its metabolite, 1-OH midazolam, and pioglitazone and its metabolite, pioglitazone M4 were evaluated by validated bioanalytical assays on each of dosing occasions of midazolam or pioglitazone.

The PK results showed that once daily dosing of relacorilant increased the plasma exposures ($AUC_{inf}$) of midazolam and its metabolite by >8-fold, relative to midazolam alone, confirming potent inhibition of CYP3A4 in vivo (Table 1). However, the PK results also showed that once daily dosing of relacorilant did not increase the plasma exposures of pioglitazone or its metabolite, indicating a lack of an inhibitory effect of relacorilant on CYP2C8 (Table 2). Although CYP2C8 inhibition by relacorilant had been prviously observed in vitro, the results of the clinical drug interaction study demonstrated that relacorilant does not inhibit CYP2C8 in vivo. e

TABLE 1

Statistical Comparisons of Plasma Midazolam and its Metabolite Pharmacokinetic Parameters: Day 14 (Treatment D) vs Day 1 (Treatment A) (PK Population)

| | Test (Day 14) Treatment D | | Reference (Day 1) Treatment A | | Ratio of | 90% |
|---|---|---|---|---|---|---|
| Parameter (unit) | Geometric LSM | n | Geometric LSM | n | Geometric LSMs (%) | Confidence Intervals |
| Midazolam | | | | | | |
| $C_{max}$ (ng/mL) | 36.85 | 26 | 11.85 | 27 | 310.98 | 271.96-355.61 |
| $AUC_{0-tz}$ (ng · h/mL) | 271.5 | 26 | 30.91 | 27 | 878.43 | 762.70-1011.7 |
| $AUC_{inf}$ (ng · h/mL) | 294.7 | 26 | 33.01 | 25 | 892.81 | 774.67-1029.0 |
| 1-OH midazolam | | | | | | |
| $C_{max}$ (ng/mL) | 6.657 | 26 | 4.038 | 27 | 164.86 | 139.84-194.35 |
| $AUC_{0-tz}$ (ng · h/mL) | 74.56 | 26 | 9.360 | 27 | 796.64 | 695.61-912.35 |
| $AUC_{inf}$ (ng · h/mL) | 83.72 | 26 | 10.28 | 26 | 814.51 | 712.14-931.60 |

ANOVA, analysis of variance;
$AUC_{inf}$, AUC from time 0 extrapolated to infinity;
$AUC_{0-tz}$, AUC from time 0 until the time of the last measurable concentration;
$C_{max}$, maximum plasma concentration;
CV %, coefficient of variation;
LSM, least squares mean.
Treatment A: Single oral dose of 2.5 mg midazolam hydrochloride administered on Day 1 (Reference).
Treatment D: Single oral dose of 2.5 mg midazolam hydrochloride and 350 mg relacorilant administered on Day 14 (Test).
Parameters were ln-transformed prior to analysis.
Geometric LSMs were calculated by exponentiating the LSMs from the ANOVA.
Ratio of Geometric LSMs = 100 * (Test/Reference); where Test is Treatment d and Reference is Treatment A.

TABLE 2

Statistical Comparisons of Plasma Pioglitazone and its Metabolite Pharmacokinetic Parameters: Day 15 (Treatment E) vs Day 2 (Treatment B) (PK Population)

| | Test (Day 15) Treatment E | | Reference (Day 2) Treatment B | | Ratio of | 90% |
|---|---|---|---|---|---|---|
| Parameter (unit) | Geometric LSM | n | Geometric LSM | n | Geometric LSMs (%) | Confidence Intervals |
| Pioglitazone | | | | | | |
| $C_{max}$ (ng/mL) | 376.5 | 26 | 483.8 | 27 | 77.82 | 69.65-86.96 |
| $AUC_{0-tz}$ (ng · h/mL) | 3953 | 26 | 5290 | 27 | 74.71 | 68.06-82.02 |
| $AUC_{inf}$ (ng · h/mL) | 4047 | 25 | 5408 | 27 | 74.83 | 68.11-82.21 |
| Pioglitazone M4 | | | | | | |
| $C_{max}$ (ng/mL) | 253.9 | 26 | 237.3 | 27 | 106.99 | 99.70-114.81 |
| $AUC_{0-tz}$ (ng · h/mL) | 10460 | 26 | 10460 | 27 | 99.97 | 94.80-105.43 |
| $AUC_{inf}$ (ng · h/mL) | 12590 | 25 | 12890 | 26 | 97.68 | 92.98-102.62 |

ANOVA, analysis of variance;
$AUC_{inf}$, AUC from time 0 extrapolated to infinity;
$AUC_{0-tz}$, AUC from time 0 until the time of the last measurable concentration;
$C_{max}$, maximum plasma concentration;
CV %, coefficient of variation;
LSM, least squares mean.
Treatment B: Single oral dose of 15 mg of pioglitazone hydrochloride (Reference).
Treatment E: Single oral dose of 15 mg of pioglitazone hydrochloride and 350 mg relacorilant administered on Day 15 followed by oral doses of 350 mg relacorilant administered QD on Days 16 and 17 (Test).
Parameters were ln-transformed prior to analysis.
Geometric LSMs were calculated by exponentiating the LSMs from the ANOVA.
Ratio of Geometric LSMs = 100 * (Test/Reference); where Test is Treatment E and Reference is Treatment B.

Example 3. Administration of Relacorilant and Nab-Paclitaxel to Patients with Advanced Pancreatic Cancer The combination of relacorilant and nab-paclitaxel has been evaluated in patients with advanced solid tumors. As the elimination of nab-paclitaxel is primarily mediated by both CYP3A4 and CYP2C8, the study was specifically designed to include a 1-week nab-paclitaxel lead-in (1 dose of nab-paclitaxel on Day 1) and a 1-week relacorilant lead-in (relacorilant daily for 7 days) before the start of Cycle 1) to assess the potential for a drug-drug interaction. An interaction would be expected because relacorilant was shown to be a potent dual inhibitor of CYP3A and CYP2C8 in vitro. The PK results from this study lead-in showed an increase in nab-paclitaxel exposures (AUC~80% higher) when administered in combination with relacorilant relative to nab-paclitaxel alone (Table 3). This small AUC increase is surprisingly low in view of the greater increases predicted by the in vitro potent, dual inhibition of both CYP2C8 and CYP3A4.

TABLE 3

Mean Pharmacokinetic Parameters for Nab-Paclitaxel Alone or in Combination with Relacorilant

| PK Parameter | Nab-paclitaxel 80 mg/m$^2$ Alone Mean (% CV) (Lead-In Day 1) N = 14 | Nab-paclitaxel 80 mg/m$^2$ in Combination with Relacorilant 100 mg Mean (% CV) (Cycle, 1 Day 8) N = 24 |
|---|---|---|
| AUC (ng · h/mL) | 2530 (28) | 4550 (97) |
| $C_{max}$ (ng/mL) | 3250 (45) | 3230 (81) |

Source: Study CORT125134-550

All patents, patent publications, publications, and patent applications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of treating cancer according to a 28-day cycle of intermittent paclitaxel and relacorilant administration, wherein said 28-day cycle begins on day0, wherein said cancer comprises a solid tumor, comprising the following administrations to a patient in need of treatment for said cancer: a) administering an effective oral dose of relacorilant of between about 75 milligrams (mg) to about 200 mg on day 0, day 7, and day 14 of said 28-day cycle of intermittent paclitaxel and relacorilant administration; and then, b) administering, on day 1, day 8, and day 15 of said 28-day cycle of intermittent paclitaxel and relacorilant administration, an effective oral dose of relacorilant of between about 75 mg to about 200 mg and an effective dose of paclitaxel that is reduced by about 20% to about 35% from the paclitaxel single agent dose of about 100 mg/m$^2$ to about 125 mg/m$^2$, wherein said single agent dose is the paclitaxel dose to be administered when paclitaxel is administered without other pharmaceutical agents; and then, c) administering, on day 2, day 9 and day 16 of said 28-day cycle of intermittent paclitaxel and relacorilant administration an effective oral dose of relacorilant of between about 75 mg to about 200 mg, wherein steps a), and b), and c) are intermittent administration steps in which paclitaxel administration is performed on days 1, 8, and 15 of said 28-day cycle, and in which relacorilant administration is performed on the day before, the day of, and the day after said paclitaxel administration, effective to provide the patient with an effective level of relacorilant and an effective level of paclitaxel at the same time, whereby the cancer comprising a solid tumor is treated according to a 28-day cycle of intermittent paclitaxel and relacorilant administration.

2. The method of claim 1, wherein said effective dose of paclitaxel is reduced from said single agent dose of paclitaxel by an amount selected from about 20%, about 25%, about 30%, and about 35%, when co-administered with relacorilant.

3. The method of claim 1, wherein said effective dose of paclitaxel is reduced from said single agent dose of paclitaxel to an effective dose of paclitaxel selected from about 72 mg/m$^2$, about 75 mg/m$^2$, about 80 mg/m$^2$, about 83 mg/m$^2$, about 88 mg/m$^2$, about 94 mg/m$^2$, and about 96 mg/m$^2$ of paclitaxel.

4. The method of claim 1, wherein paclitaxel is in the form of nab-paclitaxel.

5. The method of claim 1, wherein said effective oral dose of relacorilant is selected from 75 mg, 100 mg, 125 mg, 150 mg, 175 mg, and 200 mg of relacorilant.

6. The method of claim 1, wherein said cancer is selected from ovarian cancer, pancreatic cancer, prostate cancer, esophageal cancer, and melanoma.

7. The method of claim 1, wherein paclitaxel is in the form of nab-paclitaxel, and wherein the dose of nab-paclitaxel is selected from about 60 mg/m$^2$, about 72 mg/m$^2$, about 75 mg/m$^2$, about 80 mg/m$^2$, and about 83 mg/m$^2$ of nab-paclitaxel administered by intravenous infusion on days 1, 8 and 15 of said 28-day cycle.

8. A method of treating cancer according to a 28-day cycle of intermittent paclitaxel and relacorilant administration, wherein said 28-day cycle begins on day0, wherein said cancer comprises a solid tumor, comprising the following administrations to a patient in need of treatment for said cancer: a) administering an effective oral dose of relacorilant of between about 75 milligrams (mg) to about 200 mg on day 0, day 7, and day 14 of said 28-day cycle of intermittent paclitaxel and relacorilant administration; and then, b) administering an effective oral dose of relacorilant of between 75 mg to about 200 mg and an effective dose of paclitaxel of between about 60 mg/m$^2$ to about 95 mg/m$^2$, on day 1, day 8, and day 15 of said 28-day cycle of intermittent paclitaxel and relacorilant administration, and then c) administering an effective oral dose of relacorilant of between about 75 mg to about 200 mg on day 2, day 9 and day 16 of said 28-day cycle of intermittent paclitaxel and relacorilant administration, wherein steps a), and b), and c) are intermittent administration steps in which paclitaxel administration is performed on days 1, 8, and 15 of said 28-day cycle, and in which relacorilant administration is performed on the day before, the day of, and the day after said paclitaxel administration, at times effective to provide the patient with an effective level of relacorilant and an effective level of paclitaxel at the same time, whereby the cancer comprising a solid tumor is treated according to a 28-day cycle of intermittent paclitaxel and relacorilant administration.

9. The method of claim 8, wherein said paclitaxel is in the form of nab-paclitaxel.

10. The method of claim 8, wherein said effective dose of paclitaxel is selected from about 60 $mg/m^2$, about 65 $mg/m^2$, about 70 $mg/m^2$, about 75 $mg/m^2$, about 80 $mg/m^2$, about 85 $mg/m^2$, about 90 $mg/m^2$, and about 95 $mg/m^2$ of paclitaxel.

11. The method of claim 8, wherein said effective oral dose of relacorilant is selected from 75 mg, 100 mg, 125 mg, 150 mg, 175 mg, and 200 mg of relacorilant.

12. The method of claim 8, wherein said cancer is selected from ovarian cancer, pancreatic cancer, prostate cancer, esophageal cancer, and melanoma.

13. The method of claim 8, wherein paclitaxel is in the form of nab-paclitaxel, wherein the dose of nab-paclitaxel is selected from about 60 $mg/m^2$, about 72 $mg/m^2$, about 75 $mg/m^2$, about 80 $mg/m^2$, and about 83 $mg/m^2$ of nab-paclitaxel administered by intravenous infusion on days 1, 8 and 15 of said 28-day cycle.

* * * * *